(12) United States Patent
Dodd et al.

(10) Patent No.: US 6,562,824 B2
(45) Date of Patent: May 13, 2003

(54) DIHYDROPYRIDINE SOFT DRUGS, AND RELATED COMPOSITIONS AND METHODS

(75) Inventors: John H. Dodd, Stockton, NJ (US); James L. Bullington, Hamilton Square, NJ (US); Daniel A. Hall, Somerset, NJ (US); James R. Henry, Indianapolis, IN (US); Kenneth C. Rupert, South Orange, NJ (US)

(73) Assignee: Ortho-McNeil Pharmaceutical, Inc., Raritan, NJ (US)

( * ) Notice: Subject to any disclaimer, the term of this patent is extended or adjusted under 35 U.S.C. 154(b) by 0 days.

(21) Appl. No.: 09/847,228

(22) Filed: May 2, 2001

(65) Prior Publication Data

US 2002/0133018 A1 Sep. 19, 2002

Related U.S. Application Data

(60) Provisional application No. 60/207,915, filed on May 30, 2000.

(51) Int. Cl.$^7$ .................. A61K 31/4965; A61K 31/497; C07D 403/14; C07D 213/80; C07D 213/22
(52) U.S. Cl. .................. 514/252.03; 514/277; 544/238; 546/321; 546/322; 546/329; 546/257; 546/258
(58) Field of Search ........................... 514/252.03, 277, 514/252.02; 544/238; 546/322, 321, 329, 257, 258

(56) References Cited

U.S. PATENT DOCUMENTS

| | | | |
|---|---|---|---|
| 4,285,955 A | 8/1981 | Wehinger et al. | 424/266 |
| 4,483,985 A | 11/1984 | Wehinger et al. | 544/131 |
| 4,532,248 A | 7/1985 | Francjowiak et al. | 514/302 |
| 4,845,225 A | 7/1989 | Schwender et al. | 546/114 |
| 4,879,384 A | 11/1989 | Schwender et al. | 546/115 |
| 5,075,440 A | 12/1991 | Wustrow et al. | 540/468 |
| 5,708,177 A | 1/1998 | Straub | 546/257 |
| 6,017,965 A | 1/2000 | Mueller et al. | 514/649 |

FOREIGN PATENT DOCUMENTS

| | | | |
|---|---|---|---|
| JP | 58-201764 | | 11/1983 |
| WO | 9323082 | * | 11/1993 |
| WO | 9413275 | * | 6/1994 |
| WO | WO 99/12572 A1 | | 3/1999 |

OTHER PUBLICATIONS

CAS Abstr. 125:86502–1996:428431.*
CAS Abstr. 105:42769–1986:442769.*
CAS Abstr. 107:190351–1987:590351.*
CAS Abstr. 103:154142–1985:554142.*
CAS Abstr. 100:22580–1984:22580.*
CAS Abstr. 90:1799140–1979:179914.*
CAS Abstr. 82:170710–1975:170710.*
CAS Abstr. 70:87580–1969:87580.*

Bossert, Friedrich et al.; "1,4–dihydropyridine–3,5–dicarboxylates", Chem. Abstr. 70:87580, also cited as ZA 680 1484 dated Aug. 1968.*

Yiu, et al.: "Synthesis, Biological Evaluation, Calcium Channel Antagonist Activity, and Anticonvulsant Activity of Felodipine coupled to a Dihydrophridine–pyridinum Salt Redox Chemical Delivery System", J. Med. Chem., 1996, pp. 4576–82, vol. 39, No. 23, XP002184797.

Pagani, G., Probes for Conjugation of the Sulphonyl Group: Thiopyrao[3,2–b]Quinoline1,1–Dioxides, J. Chem. Amer. Soc., 1967, p. 1392–1397.

Lee, Henry, et al., "Recent Advances In Prodrugs and Antedrugs", Current Opinions In Drug Discovery & Development, 1998, vol. 1, No. 2 pp. 235–244.

Biggadike, Keith, et al., "Selective Plasma Hydrolysis of Glucocorticoid y–Lactones Cyclic Carbonates by the Enzyme Paraoxanase: An Ideal Plasma Inactivation Mechanism", J. Med. chem 2000, 43, pp. 19–21.

Edema, Jilles, et al., "Cesium Dithioate Bsed Syntheses of Keto–Funtionalized Thio–Crown Ethers Employung the Novel Building Block 1,3–Dimercaptoacetone. Molecular Structures of 2,5,9, 12–Tetrathia–7–oo–(13)–m–Benzenophane and 1,4,7,10, 13–Pentathiacyclohexadecan–15–One", J. Org. Chem. 1993 pp. 5624–5627.

Howard, E.G., et al. "The Chemistry of Some 5–m–Dithianones and Dithiacycloalkanones", vol. 82 pp. 158–164) (1959) J. Americ. Chem. Soc.

Eistert, Bernd, et al., "Synthesen and Umsetzungen der Thiacyclanon–1, I–Dioxide Mit Diazoalkanen", Chem. Ber. 110 pp. 1069–1085 (1977).

Mason, K.G., et al., "Butadiene Sulphone Chemistry, Part II. 3–Oxotetrahydrothiophen Dioxide and Its Reactions", J. Chem. Soc. pp. 2171–2176 (1967).

Prokai–Tatrai, K., et al. "Brain–Targeted Delivery of a Leucine–Enkephalin Analogue b) Retrometabolic Design", K/. 1996 pp. 4775–4782.

Fehnel, Edward A., Thiapyran Derivatives, III, The Preparation, Properties and Reactions of Dihydrothiapyran I,I–Dioxide, J. Amer. Chem. Soc. 73 (1951) p. 1569–1574.

PCT International Search Report PCT/US01/14309 dated May 6, 2002.

* cited by examiner

Primary Examiner—Richard L. Raymond
Assistant Examiner—Sudhaker B. Patel

(57) ABSTRACT

This invention relates to novel dihydropyridine soft drugs of the formula $\Phi OOR_1$, where $\Phi$ is a dihydropyridine moiety. These compounds are useful as calcium channel antagonists with cardiovascular, antiasthmatic and antibronchoconstriction activity. Use of such soft drug analogs permits the administration of greater doses of the claimed dihydropyridine compounds without intolerable systemic effects. Thus, this invention also provides pharmaceutical compositions, as well as methods, for preventing and treating disorders such as hypersensitivity, allergy, asthma, bronchospasim, dysmenorrhea, esophageal spasm, glaucoma, premature labor, urinary tract disorders, gastrointestinal motility disorders and cardiovascular disorders, while avoiding unwanted systemic effects.

11 Claims, No Drawings

DIHYDROPYRIDINE SOFT DRUGS, AND RELATED COMPOSITIONS AND METHODS

This application claims the benefit under 35 U.S.C. §119(e) of prior application Serial No. 60/207,915 filed on May 30, 2000.

FIELD OF THE INVENTION

This invention relates to novel dihydropyridine soft drugs and related pharmaceutical compositions useful in treating conditions such as hypersensitivity, allergy, asthma, bronchospasm, dysmenorrhea, esophageal spasm, glaucoma, premature labor, urinary tract disorders, gastrointestinal motility disorders and cardiovascular disorders.

BACKGROUND OF THE INVENTION

Dihydropyridines

Dihydropyridines inhibit L-type voltage-sensitive $Ca^{2+}$ channels and have effects on vascular smooth muscle such as dilating blood vessels and lowering blood pressure (U.S. Pat. No. 6,017,965 to Mueller et al.). U.S. Pat. No. 5,708,177 to Straub discloses a process for the preparation of optically active ortho-substituted 4-aryl- or heteroaryl-1,4-dihydropyridines by oxidation and subsequent reduction from their opposite enantiomers. U.S. Pat. No. 5,075,440 to Wustrow et al. discloses pyrido[2,3-f][1,4]thiazepiries and pyrido[3,2-b][1,5]benzothiazepines which are useful as calcium channel antagonists with cardiovascular, antiasthmatic and antibroncho constriction activity. U.S. Pat. Nos. 4,879,384 and 4,845,225, both to Schwender and Dodd, disclose substituted thiacycloalkeno [3,2-b]pyridines which are also useful as calcium channel antagonists with cardiovascular, antiasthmatic and antibronchoconstrictor activity. U.S. Pat. Nos. 4,285,955 and 4,483,985 to Wehinger et al. disclose acyclic sulfone substitution on simple dihydropyridines which possess calcium channel antagonist activity. U.S. Pat. No. 4,532,248 to Franckowiak et al. discloses a broad genus of dihydropyridines, including cyclic sulfones fused to a dihydropyridine nucleus. Cardiotonic activity is disclosed for the entire genus; however, these compounds are not calcium channel blockers. G. P. A. Pagani discloses 10-Phenyl-2H-thiopyranol[3,2-b]quinolines in J. Chem. Soc. Perkin Trans. 2, 1392 (1974). Many of these dihydropyridine drugs remain active after they enter the blood stream causing undesired systemic effects such as low blood pressure. Such side effects can limit the degree to which therapeutically effective doses of dihydropyridine drugs can be administered.

Soft Drugs

"Soft drugs" (also known as "antedrugs") are biologically active drugs which are metabolically inactivated after they achieve their therapeutic role at their designed site of action. The use of soft drugs, instead of their non-inactivatable analogs, can avoid unwanted side effects.

No dihydropyridine soft drugs are known. However, soft drugs of non-dihydropyridine compounds are known generally (see, for example, Lee et al., 1998, Curr. Opin. Drug Disc. Dev. 1: 235–44). Plasma-labile soft drugs include, for example, carboxylic ester and thioester derivatives. Biggadike et al. report that incorporation of a γ-lactone or cyclic carbonate moiety onto the glucocorticoid nucleus provides compounds which are rapidly inactivated via plasma hydrolysis (J. Med. Chem. 43:19–21, 2000). U.S. Pat. Nos. 4,540,564 and 5,389,623 (both to Bodor) disclose drugs linked to dihydropyridine moieties which can enter the brain, where they are oxidized to a charged pyridinium species which is trapped in the brain.

Prokai-Tatra, J. M., Chem, Vol. 39, p. 4777 (1996) teaches that a leucine-enkephalin analogue can be modified with a chemical delivery system which is based on a retrometabolic drug design. The enkephaklin analogue is derivatized with a dihydropyricline moiety at the N-terminus and a lipophilic moiety at the C-terminus. After intravenous administration of the conjugate, an analgesic response is observed. It is postulated that the lipophilic modification at the C-terminus enables penetration into the central nervous system, while the dihydropyridine moiety undergoes oxidative transformation to generate a charged moiety which restricts the peptides from entering the circulatory system.

WO 99/12572 (Bodor et al.) provides peptide derivatives designed to deliver peptides having growth factor inhibitory activity (somatostatin analogs in particular) to the retina by sequential metabolism. The peptide derivatives, which comprise a dihydropyridine:pyridinium salt-type redox targetor moiety, a bulky lipophilic moiety and an amino acid/dipeptide/tripeptide spacer, have use in the prevention and treatment of diabetic retinopathy.

SUMMARY OF THE INVENTION

This invention provides novel dihydropyridine soft drugs of Formula I as defined hereinbelow,

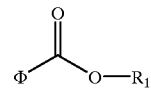

I as well as methods for making same. This invention also provides a pharmaceutical composition comprising the instant compound and a pharmaceutically acceptable carrier.

This invention further provides a method of treating a subject suffering from a disorder whose alleviation is mediated by the reduction of calcium ion influx into cells whose actions contribute to the disorder, which method comprises administering to the subject a therapeutically effective dose of the instant pharmaceutical composition.

This invention still further provides a method of inhibiting in a subject the onset of a disorder whose alleviation is mediated by the reduction of calcium ion influx into cells whose actions contribute to the disorder, which method comprises administering to the subject a prophylactically effective dose of the instant pharmaceutical composition.

Finally, this invention provides an apparatus for administering to a subject the instant pharmaceutical composition, comprising a container and the pharmaceutical composition therein, whereby the container has a means for delivering to the subject a therapeutic and/or prophylactic dose of the pharmaceutical composition.

DETAILED DESCRIPTION OF THE INVENTION

This invention provides novel dihydropyridine soft drug analogs. These soft drugs are characterized by a chemically labile moiety bound to an ester group in turn bound to the dihydropyridine ring structure. The instant soft drugs permit the dihydropyridine moieties thereof to exert their effect locally, and to subsequently be metabolized in the blood stream, thereby reducing unwanted systemic effects (e.g. low blood pressure). Use of such soft drugs permits the administration of greater doses of dihydropyridine compounds without subjecting the subject to intolerable systemic effects.

Specifically, this invention provides a compound of Formula I,

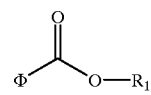

I or a pharmaceutically acceptable salt thereof, wherein (a) Φ is a dihydropyridine ring-containing moiety, which moiety, is bound to the carbonyl carbon of Formula (I) via a carbon atom in the meta position with respect to the pyridine ring nitrogen atom; and (b) $R_1$ is selected from -alkyl-OH, alkylamine, lactone, cyclic carbonate, alkyl-substituted cyclic carbonate, aryl-substituted cyclic carbonate, -aryl-C(O)OR', -alkyl-aryl-C(O)OR', -alkyl-OC(O)R', -alkyl-C(O)R', -alkyl-C(O)OR', -alkyl-N(R")C(O)R', and -alkyl-N(R") C(O)OR', wherein R' and R" are independently selected from hydrogen, amino, alkyl, aryl, aryl-fused cycloalkyl and heterocyclyl, the amino, alkyl, aryl, aryl-fused cycloalkyl and heterocyclyl being optionally substituted with halogen, cyano, $NO_2$, lactone, amino, alkylamino, aryl-substituted alkylamino, amide, carbamate, carbamoyl, cyclic carbonate, alkyl, halogen-substituted alkyl, arylalkyl, alkoxy, heterocyclyl and/or aryl (the aryl being optionally substituted with OH, halogen, cyano, $NO_2$, alkyl, amino, dimethylamino, alkoxy, alkylsulfonyl, $C_{1-4}$ carboalkcxy, alkylthio and/or trifluoromethyl).

In one embodiment of the instant invention, $R_1$ is selected from -alkyl-OH, alkylamine, lactone, cyclic carbonate, alkyl- or aryl-substituted cyclic carbonate, -aryl-C(O)OR', -alkyl-aryl-C(O)OR', -alkyl-C(O)R', -alkyl-N(R")C(O)R', and -alkyl-N(R")C(O)OR'. In a preferred embodiment of the compounds of Formula I, $R_1$ is -alkyl-aryl-C(O)OR' or -alkyl-N(R")C(O)R'. In another preferred embodiment of the compounds of Formula I, $R_1$ is -alkyl-OC(O)R' or -alkyl-C(O)OR'. In yet another preferred embodiment of the compounds of Formula I, $R_1$ is selected from —$(CH_2)_2$OC(O)CH($CH_2CH_3$)$_2$, —$(CH_2)_2$OC(O)CH($CH_3$)$_2$, —$(CH_2)_2$OC(O)PH—OCH($CH_3$)$_2$, —$CH_2$OC(O)$CH_2$N($CH_3$)$CH_2$PH, —$CH_2$OC(O)$CH_2$—PH—N($CH_3$)$_2$, and $CH_2$OC(O)CH($CH_2$)$_6$.

Compounds of Formulae Ia through Ih are exemplary of the compounds of Formula I. Specifically, this invention provides compounds of Formula Ia,

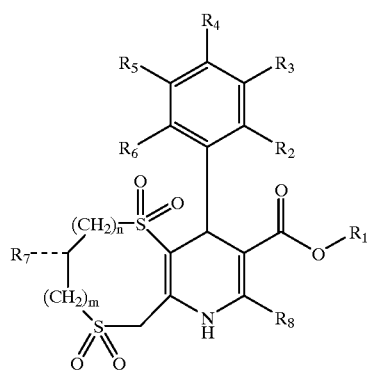

Ia wherein $R_1$ is as described above, and (a) $R_2$, $R_3$, $R_4$, $R_5$ and $R_6$ are independently selected from hydrogen, OH, halogen, cyano, $NO_2$, alkyl, $C_{1-8}$ alkoxy, $C_{1-8}$ alkylsulfonyl, $C_{1-4}$ carboalkoxy, $C_{1-8}$ alkylthio, difluoromethoxy, difluoromethylthio, trifluoromethyl and oxadiazole (formed by $R_2$ and $R_3$);

(b) $R_7$ is connected to the bis-sulfone ring via a single or double bond, as applicable, and is selected from hydrogen, alkylhydroxy, alkenyl, amino, phenyl, benzyl, $C_{1-8}$ straight or branched alkyl, trifluoromethyl, alkoxymethyl, $C_{3-7}$ cycloalkyl, substituted benzyl, formyl, acetyl, t-butyloxy carbonyl, propionyl, substituted alkyl and R'"$CH_2C=O$, wherein (i) the substituted benzyl is substituted with halogen, trifluoromethyl, $C_{1-8}$ straight and/or branched alkyl or $C_{1-8}$ alkoxy, (ii) the substituted alkyl is substituted with amino, dialkyl amino, $C_{1-8}$ alkoxy, hydroxy and/or halogen, and (iii) R'" is amino, dialkyl amino, $C_{1-8}$ alkoxy, hydroxy or halogen;

(c) $R_8$ is selected from hydrogen, amino, alkyl, aryl, trifluoromethyl, alkoxymethyl, 2-thieno and 3-thieno; and (d) m, n, and their sum are each an integer from 0 to 4.

This invention also provides compounds of Formula Ib,

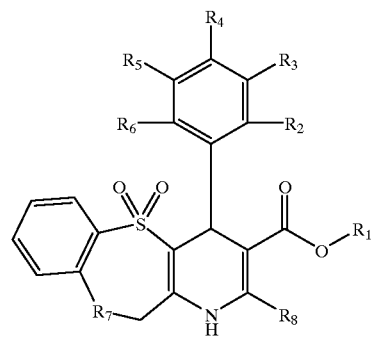

Ib wherein $R_1$ is as described above, and (a) $R_2$, $R_3$, $R_4$, $R_5$ and $R_6$ are independently selected from hydrogen, OH, halogen, cyano, $NO_2$, alkyl, $C_{1-8}$ alkoxy, $C_{1-8}$ alkylsulfonyl, $C_{1-4}$ carboalkoxy, $C_{1-8}$ alkylthio, difluoromethoxy, difluoromethylthio, trifluoromethyl and oxadiazole (formed by $R_2$ and $R_3$);

(b) $R_7$ is SO or $SO_2$; and (c) $R_8$ is selected from hydrogen, amino, alkyl, aryl, trifluoromethyl, alkoxymethyl, 2-thieno and 3-thieno.

In one embodiment of Formula Ib, $R_2$, $R_3$, $R_4$, $R_5$ and $R_6$ are independently selected from hydrogen, halogen, trifluoromethyl and $NO_2$, and $R_8$ is methyl.

This invention also provides compounds of Formula Ic,

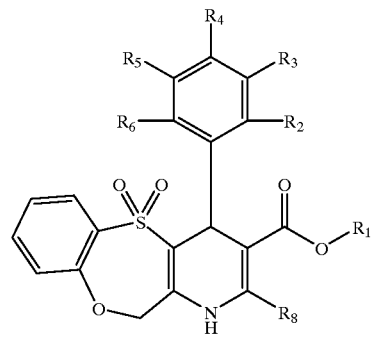

Ic wherein $R_1$ is as described above, and (a) $R_2$, $R_3$, $R_4$, $R_5$ and $R_6$ are independently selected from hydrogen, OH, halogen, cyano, $NO_2$, alkyl, $C_{1-8}$ alkoxy, $C_{1-8}$ alkylsulfonyl, $C_{1-4}$ carboalkoxy, $C_{1-8}$ alkylthio, difluoromethoxy, difluoromethylthio, trifluoromethyl and oxadiazole (formed by $R_2$ and $R_3$); and (b) $R_8$ is selected from hydrogen, amino, alkyl, aryl, trifluoromethyl, alkoxymethyl, 2-thieno and 3-thieno.

In one embodiment of Formula Ic, $R_8$ is methyl and $R_2$, $R_3$, $R_4$, $R_5$ and $R_6$ are independently selected from hydrogen, halogen, trifluoromethyl, and $NO_2$.

This invention also provides compounds of Formula Id,

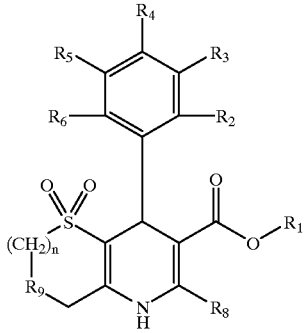

Id wherein $R_1$ is as described above, and (a) $R_2$, $R_3$, $R_4$, $R_5$ and $R_6$ are independently selected from hydrogen, OH, halogen, cyano, $NO_2$, alkyl, $C_{1-8}$ alkoxy, $C_{1-8}$ alkylsulfonyl, $C_{1-4}$ carboalkoxy, $C_{1-8}$ alkylthio, difluoromethoxy, difluoromethylthio, trifluoromethyl and oxadiazole (formed by $R_2$ and $R_3$);

(b) $R_8$ is selected from hydrogen, amino, alkyl, aryl, trifluoromethyl, alkoxymethyl, 2-thieno and 3-thieno; and (c) $R_9$ is oxygen or sulfur.

In one embodiment of Formula Id, $R_9$ is oxygen. In a further embodiment, $R_8$ is methyl, and $R_2$, $R_3$, $R_4$, $R_5$ and $R_6$ are independently selected from hydrogen, halogen, trifluoromethyl and $NO_2$.

This invention also provides compounds of Formula Ie,

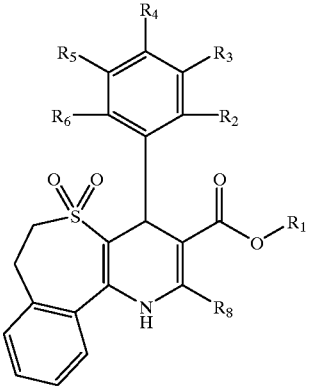

Ie wherein $R_1$ is as described above, and (a) $R_2$, $R_3$, $R_4$, $R_5$ and $R_6$ are independently selected from hydrogen, OH, halogen, cyano, $NO_2$, alkyl, $C_{1-8}$ alkoxy, $C_{1-8}$ alkylsulfonyl, $C_{1-4}$ carboalkoxy, $C_{1-8}$ alkylthio, difluoromethoxy, difluoromethylthio, trifluoromethyl and oxadiazole (formed by $R_2$ and $R_3$); and (b) $R_8$ is selected from hydrogen, amino, alkyl, aryl, trifluoromethyl, alkoxymethyl, 2-thieno and 3-thieno.

In one embodiment of Formula Ie, $R_8$ is methyl and $R_2$, $R_3$, $R_4$, $R_5$ and $R_6$ are independently selected from hydrogen, halogen, trifluoromethyl and $NO_2$.

This invention also provides compounds of Formula If,

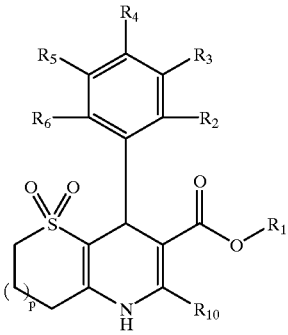

If wherein $R_1$ is as described above, and (a) $R_2$, $R_3$, $R_4$, $R_5$ and $R_6$ are independently selected from hydrogen, OH, halogen, cyano, $NO_2$, alkyl, $C_{1-8}$ alkoxy, $C_{1-8}$ alkylsulfonyl, $C_{1-4}$ carboalkoxy, $C_{1-8}$ alkylthio, difluoromethoxy, difluoromethylthio, trifluoromethyl and oxadiazole (formed by $R_2$ and $R_3$);

(b) $R_{10}$ is selected from aryl, 3-pyridyl, 2-thieno and 3-thieno; and (c) p is an integer from 1 to 5.

In one embodiment of Formula If, p is 2. In another embodiment, $R_{10}$ is selected from phenyl, 3-pyridyl, and 2-thieno. In a further embodiment, $R_2$, $R_3$, $R_4$, $R_5$ and $R_6$ are independently selected from hydrogen, OH, halogen, trifluoromethyl, and $NO_2$.

This invention also provides compounds of Formula Ig,

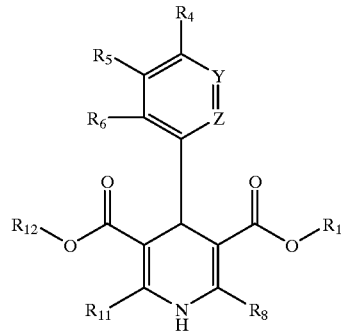

Ig wherein $R_1$ is as described above, and (a) Z is N or $CR_2$;

(b) Y is N or $CR_3$;

(c) $R_2$, $R_3$, $R_4$, $R_5$ and $R_6$ are independently selected from hydrogen, OH, halogen, cyano, $NO_2$, alkyl, $C_{1-8}$ alkoxy, $C_{1-8}$ alkylsulfonyl, $C_{1-4}$ carboalkoxy, $C_{1-8}$ alkylthio, difluoromethoxy, difluoromethylthio, trifluoromethyl and oxadiazole (formed by $R_2$ and $R_3$);

(d) $R_8$ is selected from hydrogen, amino, alkyl, aryl, trifluoromethyl, alkoxymethyl, 2-thieno and 3-thieno;

(e) $R_{11}$ is selected from hydrogen, amino, alkyl, aryl, trifluoromethyl, alkoxymethyl, 2-thieno and 3-thieno; and (f) $R_{12}$ is selected from hydrogen, -alkyl-OH, alkylamine, lactone, cyclic carbonate, alkyl-substituted cyclic carbonate, aryl-substituted cyclic carbonate, -aryl-C(O)OR', -alkyl-OC(O)R', -alkyl-C(O)R', -alkyl-C(O)OR', -alkyl-N(R")C(O)R', -alkyl-N(R")C(O)OR', -alkyl-S-R', alkyl, aryl-substituted alkyl, aryl, —(CH$_2$)$_2$N(CH$_3$)CH$_2$PH, —CH$_2$CH$_2$—N(Me)—CH$_2$— heteroaryl, 3-piperidyl, N-substituted 3-piperidyl, and N-substituted 2-pyrrolidinyl methylene, wherein
(i) R' and R" are independently selected from hydrogen, amino, alkyl, aryl, aryl-fused cycloalkyl and heterocyclyl, the amino, alkyl, aryl, aryl-fused cycloalkyl and heterocyclyl being optionally substituted with halogen, cyano, NO$_2$, lactone, amino, alkylamino, aryl-substituted alkylamino, amide, carbamate, carbamoyl, cyclic carbonate, alkyl, halogen-substituted alkyl, arylalkyl, alkoxy, heterocyclyl and/or aryl (the aryl being optionally substituted with OH, halogen, cyano, NO$_2$, alkyl, amino, dimethylamino, alkoxy, alkylsulfonyl, C$_{1-4}$ carboalkoxy, alkylthio and/or trifluoro methyl);
(ii) the alkyl may be substituted with alkoxy, C$_2$–C$_8$ alkanoyloxy, phenylacetyloxy, benzoyloxy, hydroxy, halogen, p-tosyloxy, mesyloxy, amino, carboalkoxy, and/or NR$^{IV}$R$^V$, wherein
R$^{IV}$ and R$^V$ are independently selected from hydrogen, alkyl, phenyl, benzyl and phenethyl, or R$^{IV}$ and R$^V$ together form a heterocyclic ring selected from the group consisting of piperidino, pyrrolidino, morpholino, thiomorpholino, piperazino, 2-thieno, 3-thieno and an N-substituted derivative of the heterocyclic rings (the N-substituted derivative being substituted with hydrogen, alkyl, benzyl, benzhydryl and/or phenyl optionally substituted with hydrogen, NO$_2$, halogen, alkyl, alkoxy and/or trifluoromethyl); and
(iii) the N-substituted 3-piperidyl and the N-substituted 2-pyrrolidinyl methylene are optionally substituted with alkyl or benzyl.

In one embodiment of Formula Ig, R$_{12}$ is selected from hydrogen, alkyl, and aryl-substituted alkyl. In another embodiment, R$_{12}$ is selected from hydrogen, —CH$_3$, —CH$_2$CH$_3$, —CH(CH$_3$)$_2$, —CH(CH$_3$)CH$_2$CH$_3$, —CH$_2$CH$_2$—O—CH$_3$, —CH$_2$CH$_2$—S—CH$_3$, cyclopentane, and benzyl. In two further embodiments, Z is CR$_2$ and Y is CR$_3$.

This invention also provides compounds of Formula Ih,

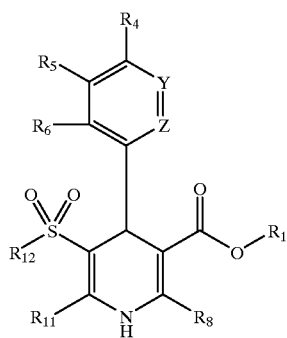

Ih wherein R$_1$ is as described above, and
(a) Z is N or CR$_2$;
(b) Y is N or CR$_3$;
(c) R$_2$, R$_3$, R$_4$, R$_5$ and R$_6$ are independently selected from hydrogen, OH, halogen, cyano, NO$_2$, alkyl, C$_{1-8}$ alkoxy, C$_{1-8}$ alkylsulfonyl, C$_{1-4}$ carboalkoxy, C$_{1-8}$ alkylthio, difluoromethoxy, difluoromethylthio, trifluoromethyl and oxadiazole (formed by R$_2$ and R$_3$);

(d) R$_8$ is selected from hydrogen, amino, alkyl, aryl, trifluoromethyl, alkoxymethyl, 2-thieno and 3-thieno;
(e) R$_{11}$ is selected from hydrogen, amino, alkyl, aryl, trifluoromethyl, alkoxymethyl, 2-thieno and 3-thieno; and
(f) R$_{12}$ is selected from hydrogen, -alkyl-OH, alkylamine, lactone, cyclic carbonate, alkyl-substituted cyclic carbonate, aryl-substituted cyclic carbonate, -aryl-C(O)OR', -alkyl-OC(O)R', -alkyl-C(O)R', -alkyl-C(O)OR', -alkyl-N(R")C(O)R', -alkyl-N(R")C(O)OR', -alkyl-S-R', alkyl, aryl-substituted alkyl, aryl, —(CH$_2$)$_2$N(CH$_3$)CH$_2$PH, —CH$_2$CH$_2$—N(Me)—CH$_2$— heteroaryl, 3-piperidyl, N-substituted 3-piperidyl, and N-substituted 2-pyrrolidinyl methylene, wherein
(i) R' and R" are independently selected from hydrogen, amino, alkyl, aryl, aryl-fused cycloalkyl and heterocyclyl, the amino, alkyl, aryl, aryl-fused cycloalkyl and heterocyclyl being optionally substituted with halogen, cyano, NO$_2$, lactone, amino, alkylamino, aryl-substituted alkylamino, amide, carbamate, carbamoyl, cyclic carbonate, alkyl, halogen-substituted alkyl, arylalkyl, alkoxy, heterocyclyl and/or aryl (the aryl being optionally substituted with OH, halogen, cyano, NO$_2$, alkyl, amino, dimethylamino, alkoxy, alkylsulfonyl, C$_{1-4}$ carboalkoxy, alkylthio and/or trifluoromethyl);
(ii) the alkyl may be substituted with alkoxy, C$_2$–C$_8$ alkanoyloxy, phenylacetyloxy, benzoyloxy, hydroxy, halogen, p-tosyloxy, mesyloxy, amino, carboalkoxy, and/or NR$^{IV}$R$^V$, wherein
R$^{IV}$ and R$^V$ are independently selected from hydrogen, alkyl, phenyl, benzyl and phenethyl, or R$^{IV}$ and R$^V$ together form a heterocyclic ring selected from the group consisting of piperidino, pyrrolidino, morpholino, thiomorpholino, piperazino, 2-thieno, 3-thieno and an N-substituted derivative of the heterocyclic rings (the N-substituted derivative being substituted with hydrogen, alkyl, benzyl, benzhydryl and/or phenyl optionally substituted with hydrogen, NO$_2$, halogen, alkyl, alkoxy and/or trifluoromethyl); and
(iii) the N-substituted 3-piperidyl and the N-substituted 2-pyrrolidinyl methylene are optionally substituted with alkyl or benzyl.

In one embodiment of Formula Ih, R$_{12}$ is aryl, and preferably phenyl. In another embodiment, Z is CR$_2$.

The following compounds are preferred embodiments of the present invention:
5H-[1,4]dithiepino[6,5-b]pyridine-8-carboxylic acid, 9-(2-chloro-6-fluorophenyl)-2,3,6,9-tetrahydro-7-methyl-, 2-(2-ethyl-1-oxobutoxy)ethyl ester, 1,1,4,4-tetraoxide;
5H-[1,4]dithiepino[6,5-b]pyridine-8-carboxylic acid, 9-(2,3-dichlorophenyl)-2,3,6,9-tetrahydro-7-methyl-, 2-(2-methyl-1-oxopropoxy)ethyl ester, 1,1,4,4-tetraoxide;
5H-[1,4]dithiepino[6,5-b]pyridine-8-carboxylic acid, 9-(2-chloro-6-fluorophenyl)-2,3,6,9-tetrahydro-7-methyl-, 2-[[4-(1-methylethoxy)lbenzoyl] oxy]ethyl ester, 1,1,4,4-tetraoxide;
5H-[1,4]dithiepino[6,5-b]pyridine-8-carboxylic acid, 9-(2-chloro-6-fluorophenyl)-2,3,6,9-tetrahydro-7-methyl-, 2-[(4-methyl-1-oxopentyl)oxy]ethyl ester, 1,1,4,4-tetraoxide;
5H-[1,4]dithiepino[6,5-b]pyridine-8-carboxylic acid, 9-(2-chloro-6-fluorophenyl)-2,3,6,9-tetrahydro-7-methyl-, 2-(2-methyl-1-oxo-3-phenylpropoxy) ethyl ester, 1,1,4,4-tetraoxide;

5H-[1,4]dithiepino[6,5-b]pyridine-8-carboxylic acid, 9-(2-chloro-6-fluorophenyl)-2,3,6,9-tetrahydro-7-methyl-, 2-(3-methyl-1-oxobutoxy)ethyl ester, 1,1,4,4-tetraoxide;

5H-[1,4]dithiepino[6,5-b]pyridine-8-carboxylic acid, 9-(2-chloro-6-fluorophenyl)-2,3,6,9-tetrahydro-7-methyl-, 2-[(cycloheptylcarbonyl)oxy]ethyl ester, 1,1,4,4-tetraoxide;

5H-[1,4]dithiepino[6,5-b]pyridine-8-carboxylic acid, 9-(2-chloro-6-fluorophenyl)-2,3,6,9-tetrahydro-7-methyl-, 2-[(3-methoxybenzoyl)oxy]ethyl ester, 1,1,4,4-tetraoxide;

5H-[1,4]dithiepino[6,5-b]pyridine-8-carboxylic acid, 9-(2-chloro-6-fluorophenyl)-2,3,6,9-tetrahydro-7-methyl-, 3-(benzoyloxy)propyl ester, 1,1,4,4-tetraoxide;

5H-[1,4]dithiepino[6,5-b]pyridine-8-carboxylic acid, 9-(2-chloro-6-fluorophenyl)-2,3,6,9-tetrahydro-7-methyl-, 2-[[(1,2,3,4-tetrahydro-2-naphthalenyl)carbonyl]oxy]ethyl ester, 1,1,4,4-tetraoxide;

5H-[1,4]dithiepino[6,5-b]pyridine-8-carboxylic acid, 9-(2-chloro-6-fluorophenyl)-2,3,6,9-tetrahydro-7-methyl-, 2-[[4-(trifluoromethyl)benzoyl]oxy]ethyl ester, 1,1,4,4-tetraoxide;

2H,6H-[1,5]dithiocino[3,2-b]pyridine-9-carboxylic acid, 10-(2-chloro-6-fluorophenyl)-3,4,7,10-tetrahydro-8-methyl-, 2-[[4-(1-methylethoxy)benzoyl]oxy] ethyl ester, 1,1,5,5-tetraoxide;

2H,6H-[1,5]dithiocino[3,2-b]pyridine-9-carboxylic acid, 10-(2-chloro-6-fluorophenyl)-3,4,7,10-tetrahydro-8-methyl-, 2-[(3-cyanobenzoyl)oxy]ethyl ester, 1,1,5,5-tetraoxide;

2H,6H-[1,5]dithiocino[3,2-b]pyridine-9-carboxylic acid, 10-(2-chloro-6-fluorophenyl)-3,4,7,10-tetrahydro-8-methyl-, 2-[(cyclohexylcarbonyl)oxy]ethyl ester, 1,1,5,5-tetraoxide;

1H-[1,5]benzodithiepino[3,2-b]pyridine-3-carboxylic acid, 4-(2-chloro-6-fluorophenyl)-4,11-dihydro-2-methyl-, 2-(acetyloxy)ethyl ester, 5,5,10,10-tetraoxide;

1H-[1,5]benzodithiepino[3,2-b]pyridine-3-carboxylic acid, 4-(2-chloro-6-fluorophenyl)-4,11-dihydro-2-methyl-, 2-(benzoyloxy)ethyl ester, 5,5,10,10-tetraoxide;

1H-[1,5]benzodithiepino[3,2-b]pyridine-3-carboxylic acid, 4-(2-chloro-6-fluorophenyl)-4,11-dihydro-2-methyl-, 2-[(cyclohexylcarbonyl)oxy]ethyl ester, 5,5,10,10-tetraoxide;

1H-[1,5]benzodithiepino[3,2-b]pyridine-3-carboxylic acid, 4-(2-chloro-6-fluorophenyl)-4,11-dihydro-2-methyl-, 2-[[(1,1-dimethylethoxy)carbonyl]amino] ethyl ester, 5,5,10,10-tetraoxide;

1H-[1,5]benzodithiepino[3,2-b]pyridine-3-carboxylic acid, 4-(2-chloro-6-fluorophenyl)-4,11-dihydro-2-methyl-, 2-aminoethyl ester, 5,5,10,10-tetraoxide;

1H-[1,5]benzodithiepino[3,2-b]pyridine-3-carboxylic acid, 4-(2-chloro-6-fluorophenyl)-4,11-dihydro-2-methyl-, tetrahydro-2-oxo-3-furanyl ester, 5,5,10,10-tetraoxide;

1H-[1,5]benzodithiepino[3,2-b]pyridine-3-carboxylic acid, 4-(2-chloro-6-fluorophenyl)-4,11-dihydro-2-methyl-, 2-(2,2-dimethyl-1-oxopropoxy)ethyl ester, 5,5,10,10-tetraoxide;

1H-[1,5]benzodithiepino[3,2-b]pyridine-3-carboxylic acid, 4-(2-chloro-6-fluorophenyl)-4,11-dihydro-2-methyl-, 2-(benzoylamino)ethyl ester, 5,5,10,10-tetraoxide;

1H-[1,5]benzodithiepino[3,2-b]pyridine-3-carboxylic acid, 4-(2-chloro-6-fluorophenyl)-4,11-dihydro-2-methyl-, 2-[[(2S)-2-(6-methoxy-2-naphthalenyl)-1-oxopropyl]oxy]ethyl ester, 5,5,10,10-tetraoxide;

1H-[1,5]benzodithiepino[3,2-b]pyridine-3-carboxylic acid, 4-(2-chloro-6-fluorophenyl)-4,11-dihydro-2-methyl-, 2-[[(2E)-1-oxo-3-phenyl-2-propenyl]oxy] ethyl ester, 5,5,10,10-tetraoxide;

5H-[1,4]oxathiepino[6,5-b]pyridine-8-carboxylic acid, 9-(2,3-dichlorophenyl)-2,3,6,9-tetrahydro-7-methyl-, (5-methyl-2-oxo-1,3-dioxol-4-yl)methyl ester, 1,1-dioxide;

5H-[1,4]oxathiepino[6,5-b]pyridine-8-carboxylic acid, 9-(2,3-dichlorophenyl)-2,3,6,9-tetrahydro-7-methyl-, (2-oxo-5-phenyl-1,3-dioxol-4-yl)methyl ester, 1,1-dioxide;

5H-[1,4]oxathiepino[6,5-b]pyridine-8-carboxylic acid, 9-(2-chlorophenyl)-2,3,6,9-tetrahydro-7-methyl-, 2-hydroxyethyl ester, 1,1-dioxide;

5H-[1,4]oxathiepino[6,5-b]pyridine-8-carboxylic acid, 9-(2-chlorophenyl)-2,3,6,9-tetrahydro-7-methyl-, 2-(2-methyl-1-oxopropoxy)ethyl ester, 1,1-dioxide;

5H-[1,4]oxathiepino[6,5-b]pyridine-8-carboxylic acid, 9-(2-chloro-6-fluorophenyl)-2,3,6,9-tetrahydro-7-methyl-, 2-(2-methyl-1-oxopropoxy)ethyl ester, 1,1-dioxide;

5H-[1,4]oxathiepino[6,5-b]pyridine-8-carboxylic acid, 9-(2-chloro-6-fluorophenyl)-2,3,6,9-tetrahydro-7-methyl-, 2-[(cyclopropylcarbonyl)oxy]ethyl ester, 1,1-dioxide;

5H-[1,4]oxathiepino[6,5-b]pyridine-8-carboxylic acid, 9-(2-chloro-6-fluorophenyl)-2,3,6,9-tetrahydro-7-methyl-, 2-(acetyloxy)ethyl ester, 1,1-dioxide;

5H-[1,4]oxathiepino[6,5-b]pyridine-8-carboxylic acid, 9-(2-chloro-6-fluorophenyl)-2,3,6,9-tetrahydro-7-methyl-, 2-[(cyclohexylcarbonyl)oxy]ethyl ester, 1,1-dioxide;

5H-[1,4]oxathiepino[6,5-b]pyridine-8-carboxylic acid, 9-(2-chloro-6-fluorophenyl)-2,3,6,9-tetrahydro-7-methyl-, 2-(benzoyloxy)ethyl ester, 1,1-dioxide;

5H-[1,4]oxathiepino[6,5-b]pyridine-8-carboxylic acid, 9-(2-chlorophenyl)-2,3,6,9-tetrahydro-7-methyl-, 3-(benzoyloxy)propyl ester, 1,1-dioxide;

3,5-pyridinedicarboxylic acid, 1,4-dihydro-2,6-dimethyl-4-(3-nitrophenyl)-, 3-methyl 5-(tetrahydro-2-oxo-3-furanyl) ester;

3,5-pyridinedicarboxylic acid, 1,4-dihydro-2,6-dimethyl-4-(3-nitrophenyl)-, 3-methyl 5-[2-(tetrahydro-2-oxo-3-furanyl)ethyl] ester;

3,5-pyridinedicarboxylic acid, 1,4-dihydro-2,6-dimethyl-4-(3-nitrophenyl)-, 3-methyl 5-[(5-methyl-2-oxo-1,3-dioxol-4-yl)methyl] ester; and 3,5-pyridinedicarboxylic acid, 1,4-dihydro-2,6-dimethyl-4-(3-nitrophenyl)-, 3-methyl 5-[(2-oxo-5-phenyl-1,3-dioxol-4-yl)methyl] ester.

Unless specified otherwise, the term "alkyl" refers to a straight, branched or cyclic substituent consisting solely of carbon and H with no unsaturation. The term "alkoxy" refers to O-alkyl where alkyl is as defined. Aryl substituents include, for example, phenyl, naphthyl, diphenyl, fluorophenyl, difluorophenyl, benzyl, benzoyloxyphenyl, carboethoxyphenyl, acetyl phenyl, ethoxyphenyl, phenoxyphenyl, hyd roxyphenyl, carboxyphenyl, trifluoromethylphenyl, methoxyethylphenyl, acetamidophenyl, tolyll, xylyl, dimethylcarbamylphenyl, —(CH$_2$)$_2$N(CH$_3$)CH$_2$PH, —CH$_2$CH$_2$—N(Me)—CH$_2$—heteroaryl and the like. The term "halo" means fluoro, chloro, bromo and iodo. The symbol "Ph" or "PH" refers to phenyl. "Independently" means that when there are more than one substituent, the substitutents may be different.

The compounds of the instant invention are asymmetric in the dihydropyridine ring at the 4-position and thus exist as optical antipodes. As such, all possible optical isomers, antipodes, enantiomers, and diastereomers resulting from additional asymmetric centers that may exist in optical antipodes, racemates and racemic mixtures thereof are also part of this invention. The antipodes can be separated by methods known to those skilled in the art such as, for example, fractional recrystallization of diastereomeric salts of enantiomerically pure acids. Alternatively, the antipodes can be separated by chromatography in a Pirkle type column.

As used herein, the phrase "pharmaceutically acceptable salt" means a salt of the free base which possesses the desired pharmacological activity of the free base and which is neither biologically nor otherwise undesirable. These salts may be derived from inorganic or organic acids. Examples of inorganic acids are hydrochloric acid, nitric acid, hydrobromic acid, sulfuric acid, and phosphoric acid. Examples of organic acids are acetic acid, propionic acid, glycolic acid, lactic acid, pyruvic acid, malonic acid, succinic acid, malic acid, maleic acid, fumaric acid, tartaric acid, citric acid, benzoic acid, cinnamic acid, mandelic acid, methanesulfonic acid, ethanesulfonic acid, p-toluenesulfonic acid, methyl sulfonic acid, salicyclic acid and the like.

The instant compounds can be prepared using readily available starting materials and reaction steps well known in the art (Edema et al. J. Org. Chem. 58: 5624–7, 1993; Howard et al., J. Amer. Chem. Soc. 82:158–64, 1960).

This invention also provides a pharmaceutical composition comprising any of the instant compounds and a pharmaceutically acceptable carrier.

Pharmaceutical compositions containing a compound of the present invention as the active ingredient in intimate admixture with a pharmaceutical carrier can be prepared according to conventional pharmaceutical techniques. The carrier may take a wide variety of forms depending on the form of preparation desired for administration, such as systemic administration including but not limited to intravenous, oral, nasal or parenteral. In preparing the compositions in oral dosage form, any of the usual pharmaceutical carriers may be employed, such as water, glycols, oils, alcohols, flavoring agents, preservatives, coloring agents, syrup and the like in the case of oral liquid preparations (for example, suspensions, elixirs and solutions), and carriers such as starches, sugars, diluents, granulating agents, lubricants, binders, disintegrating agents and the like in the case of oral solid preparations (for example, powders, capsules and tablets).

In one embodiment, the compounds of the instant invention are administered by inhalation. For inhalation administration, the compounds can be in a solution intended for administration by metered dose inhalers, or in a form intended for a dry powder inhaler or insufflator. More particularly, the instant compounds can be conveniently delivered in the form of an aerosol spray from a pressurized container, a pack or a nebuliser with the use of a suitable propellant, e.g., dichlorodifluoromethane, trichlorofluoromiethane, dichlorotetrafluoroethane, carbon dioxide or other suitable gas. The dosage unit may be determined by providing a valve to deliver a metered amount. Capsules and cartridges made of a pharmaceutically acceptable material such as gelatin for use in an inhaler or insufflator can be formulated to contain a powder mix of the compound and a suitable powder base such as lactose or starch.

Because of their ease of administration, tablets and capsules represent an advantageous oral dosage unit form wherein solid pharmaceutical carriers are employed. If desired, tablets can be sugar-coated or enteric-coated by standard techniques. For parenterals, the carrier will usually comprise sterile water, though other ingredients to aid solubility or to act as preservatives can be included. Injectable suspensions can also be prepared, wherein appropriate liquid carriers, suspending agents and the like are employed. The instant compounds can also be administered in the form of an aerosol, as discussed above.

The compounds of the present invention inhibit the uptake of calcium ions into smooth muscle cells, and therefore act to relax or prevent calcium ion-mediated contraction of smooth muscle tissue.

Thus, this invention further provides a method of treating a subject suffering from a disorder whose alleviation is mediated by the reduction of calcium ion influx into cells whose actions contribute to the disorder, which method comprises administering to the subject a therapeutically effective dose of the instant pharmaceutical composition. By way of example, in a subject suffering from asthma, the subject's airways are constricted due to inflammation of airway smooth muscle cells ("SMC's"). Reducing the calcium influx into the SMC's, whose action (i.e., inflammation) contributes to the disorder, would be expected to alleviate the disorder.

This invention still further provides a method of inhibiting in a subject the onset of a disorder whose alleviation is mediated by the reduction of calcium ion influx into cells whose actions contribute to the disorder, which method comprises administering to the subject a prophylactically effective dose of the instant pharmaceutical composition.

In one embodiment, the disorder is selected from the group consisting of hypersensitivity, allergy, asthma, bronchospasm, dysmenorrhea, esophageal spasm, glaucoma, premature labor, a urinary tract disorder, a gastrointestinal motility disorder and a cardiovascular disorder. In the preferred embodiment, the disorder is asthma. The cardiovascular disorder can be, for example, hypertension, ischemia, angina, congestive heart failure, myocardial infarction or stroke.

As used herein, "treating" a disorder means eliminating or otherwise ameliorating the cause and/or effects thereof. "Inhibiting" the onset of a disorder means preventing, delaying or reducing the likelihood of such onset.

The term "subject" includes, without limitation, any animal or artificially modified animal. In the preferred embodiment, the subject is a human.

Methods are known in the art for determining therapeutically and prophylactically effective doses for the instant pharmaceutical composition. The effective dose for administering the pharmaceutical composition to a human, for example, can be determined mathematically from the results of animal studies. In one embodiment, the instant pharmaceutical composition contains a per dosage unit (e.g., tablet, capsule, powder, injection, teaspoonful and the like) from about 0.001 to about 100 mg/kg, and preferably from about 0.01 to about 20 mg/kg of the instant compound.

This invention further provides an apparatus for administering to a subject the instant pharmaceutical composition, comprising a container and the pharmaceutical composition therein, whereby the container has a means for delivering to the subject a therapeutic and/or prophylactic dose of the pharmaceutical composition. In the preferred embodiment, the apparatus is an aerosol spray device for treating and/or preventing asthma via topical respiratory administration.

Finally, this invention provides processes for preparing the compound of Formula I.

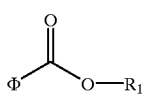

One process for preparing the compound of Formula I comprises reacting the compound of Formula 1a with $R_1Br$ or $R_1Cl$ in the presence of

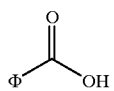

$K_2CO_3$ or $CsCO_3$ in dimethylformamide to form the compound of Formula I.

Another process for preparing the compound of Formula I comprises converting the compound of Formula 2a

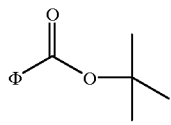

to the compound of Formula I in the presence of formic acid.

Yet another process for preparing the compound of Formula I comprises converting the compound of Formula 2b

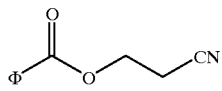

to the compound of Formula I in the presence of NaOH (aq).

This invention will be better understood by reference to the Experimental Details that follow, but those skilled in the art will readily appreciate that these are only illustrative of the invention as described more fully in the claims which follow thereafter. Additionally, throughout this application, various publications are cited. The disclosure of these publications is hereby incorporated by reference into this application to describe more fully the state of the art to which this invention pertains.

Experimental Details

A. Schemes and Syntheses

Procedures for making dihydropyridines are well documented in the art, as exemplified by Eistert et al. (Chem. Ber. 110, 1069–1085,1977), G. A. Pagani (J. Chem. Soc., Perkin Trans. 2, 1392–7, 1974), Mason et al. (J. Chem. Soc. (C) 2171–76, 1967), E. A. Fehnel (J. Amer. Chem. Soc. 74,1569–74, 1952), and M. Seiyaku (Japan Patent Application No. 58201764, 1984).

The compounds of Formula I can be made in accordance with Scheme 1, wherein Φ and $R_1$ are as described above, preferably in the presence of $K_2CO_3$ or $CsCO_3$ in an organic solvent such as dimethylformamide (DMF):

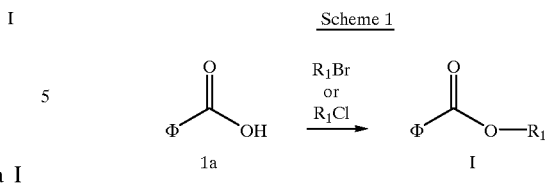

The compounds of Formula I may also be made in accordance with Scheme 2, wherein Φ and $R_1$ are as described above, preferably in the presence of formic acid or NaOH (aq), respectively:

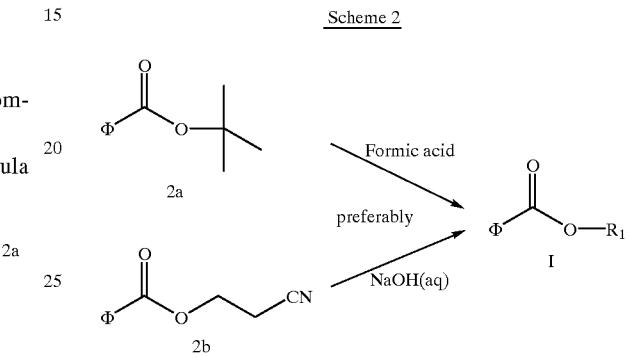

The examples below describe in greater detail the chemical syntheses of representative compounds of the present invention. The rest of the compounds disclosed herein can be prepared similarly in accordance with one or more of these methods. No attempt has been made to optimize the yields obtained in these syntheses, and it would be clear to one skilled in the art that variations in reaction times, temperatures, solvents, and/or reagents could be used to increase such yields.

EXAMPLE 1

7-methyl-9-[2-fluoro-6-chlorophenyl]-2,3,6 9-tetrahydro-1,1,4,4-tetraoxide 5H-1,4-Dithiepino[6,5-b]pyridine-8-carboxylic acid 2-(1,1-dimethylethyloxy)-2-oxoethyl ester (Compound 37)

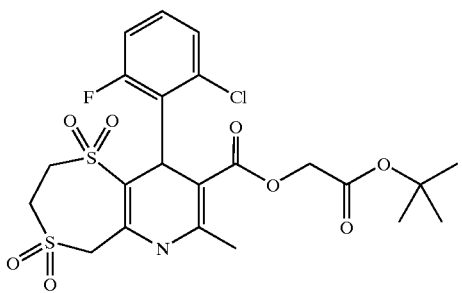

7-methyl-9-[2-fluoro-6-chlorophenyl]-2,3,6,9-tetrahydro-1,1,4,4-tetraoxide 5H-1,4-Dithiepino[6,5-b]pyridine-8-carboxylic acid (1.0 g, 2.29 mmol) was dissolved in DMF (2 mL) and potassium carbonate (0.6 g, 4.34 mmol) was added. After stirring for 15 minutes bromo t-butyl acetate (0.34 mL, 2.29 mmol) was added. After 1 hour the reaction was diluted with 50 mL of water. This mixture was stirred for 15 minutes before filtering the resulting precipitate. This solid was dissolved in 35 mL of ethyl acetate and purified on a bed of silica gel (75 mL) to give pure 7-methyl-9-[2-fluoro-6-chlorophenyl]-2,3,6,9-tetrahydro-1,1,4,4-tetraoxide 5H-1,4-dithiepino[6,5-b]pyridine-8-carboxylic acid 2-(1,1-dimethylethyloxy)-2-oxoethyl ester isolated as a colorless solid (0.81 g).

EXAMPLE 2

7-methyl-9-[2-fluoro-6-chlorophenyl]-2,3,6,9-tetrahydro-1,1,4,4tetraoxide 5H-1,4-Dithiepino[6,5-b]pyridine-8-carboxylic acid carboxymethyl ester (Compound 66)

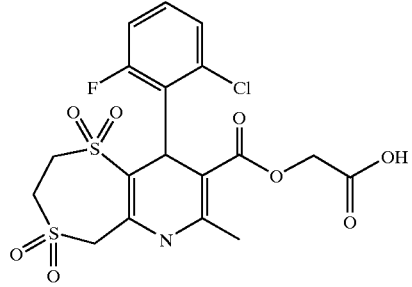

7-methyl-9-[2-fluoro-6-chlorophenyl]-2,3,6,9-tetrahydro-1,1,4,4-tetraoxide 5H-1,4-Dithiepino[6,5-b] pyridine-8-carboxylic acid 2-(1,1-dimethylethyloxy)-2-oxoethyl ester (0.7 g, 1.273 mmol) was suspended in 96% formic acid (6 mL) and stirred at 25° C. for 16 hours. The resulting solid was filtered and washed with water to give a colorless solid. This solid was dissolved in 1 N NaOH and washed with ethyl acetate to remove unreacted starting material. The aqueous layer was acidified with 1 N HCl and the resulting solid filtered and washed with water and dried. The solid was dried under vacuum at 60° C. to give 0.35 g of the 7-methyl-9-[2-fluoro-6-chlorophenyl]-2,3,6,9-tetrahydro-1,1,4,4-tetraoxide 5H-1,4-Dithiepino[6,5-b] pyridine-8-carboxylic acid carboxymethyl ester.

EXAMPLE 3

7-methyl-9-[2-fluoro-6-chlorophenyl]-2,3,6,9-tetrahydro-1,1,4,4-tetraoxide 5H-1,4-Dithiepino[6,5-b]pyridine-8-carboxylic acid carboxy-2-(1-N-methylbenzylamine)ethyl ester (Compound 42)

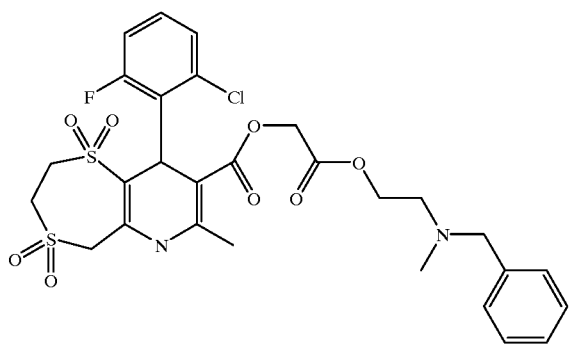

7-methyl-9-[2-fluoro-6-chlorophenyl]-2,3,6,9-tetrahydro-1,1,4,4-tetraoxide 5H-1,4-Dithiepino[6,5-b] pyridine-8-carboxylic acid carboxymethyl ester (0.278 g, 0.563 mmol) was dissolved in DMF (2 mL) and potassium carbonate (0.4 g. 2.894 mmol) was added. After stirring for 15 minutes N-(2-chloroethyl)-N-methylbenzylamine hydrochloride (0.124g, 0.563 mmol) was added. After heating the reaction to 70° C. for 60 minutes the reaction was cooled and diluted with 50 mL of water. This mixture was stirred for 15 minutes before extracting into ethyl acetate (2×50 mL). The organic layer was washed with water (3×20 mL) and dried over sodium sulfate. Evaporation of the solvent in vacuo gave an oil which was purified on silica gel eluting with ethyl acetate/hexanes (70/30). Trituration with ether gave pure 7-methyl-9-[2-fluoro-6-chlorophenyl]-2,3,6,9-tetrahydro-1,1,4,4-tetraoxide 5H-1,4-Dithiepino[6,5-b] pyridine-8-carboxylic acid carboxy-2-(1-N-methylbenzylamine)ethyl ester isolated as a colorless solid (0.077g).

EXAMPLE 4

7-methyl-9-[2-fluoro-6-chlorophenyl]-2,3,6,9-tetrahydro-1,1,4,4-tetraoxide 5H-1,4-Dithiepino[6,5-b]pyridine-8-carboxylic acid 3-benzoyloxypropyl ester (Compound 9)

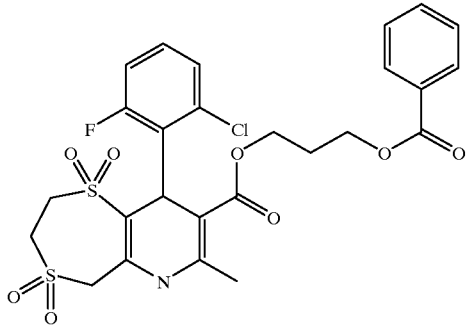

7-methyl-9-[2-fluoro-6-chlorophenyl]-2,3,6,9-tetrahydro-1,1,4,4-tetraoxide 5H-1,4-Dithiepino[6,5-b] pyridine-8-carboxylic acid 3-hydroxypropyl ester (0.179 g, 0.362 mmol), benzoyl chloride (42 μL, 0.362 mmol) and triethylamine (0.10 mL) were stirred in methylene chloride (50 mL) for 16 hours. A second portion of benzoyl chloride (42 μL, 0.362 mmol) was added to allow the reaction to go to completion. After 1 hour the reaction was diluted with methylene chloride (50 mL) and washed with 3N HCl (2×30 mL). The organic layer was dried over sodium sulfate and evaporated in vacuo to give an oil. This resulting oil was purified through a bed of silica gel (40 mL) eluting with methylene chloride to rid of excess benzoyl chloride. The product was collected by elution with ethyl acetate to give 0.12 g of 7-methyl-9-[2-fluoro-6-chlorophenyl]-2,3,6,9-tetrahydro-1,1,4,4-tetraoxide 5H-1,4-Dithiepino[6,5-b] pyridine-8-carboxylic acid 3-benzoyloxypropyl ester isolated as a colorless solid.

EXAMPLE 5

7-methyl-9-[2-fluoro-6-chlorophenyl]-2,3,6,9-tetrahydo-1,1,4,4-tetraoxide 5H-1,4-Dithiepino[6,5-b]pyridine-8-carboxlic acid 2-[1,2,3,4-tetrahydo-2-napthoyl]oxyethyl ester (Compound 10)

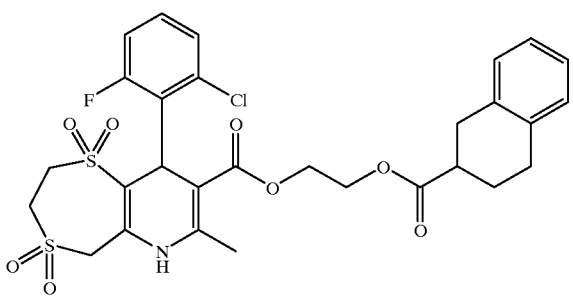

7-methyl-9-[2-fluoro-6-chlorophenyl]-2,3,6,9-tetrahydo-1,1,4,4-tetraoxide 5H-1,4-Dithiepino[6,5-b]pyridine-8-carboxlic acid 2-hydroxyethyl ester (0.3 g. 0.627 mmol) and 1,2,3,4-tetrahydo-2-napthoic acid (0.177 g, 1.00 mmol) was suspended in 6 mL of 2:1 dichloromethane/tetrahydrofuran. To this solution was added 1-(3-dimethylaminopropyl)-3-ethylcarbodiimide hydrochloride (0.36 g, 1.88 mmol) and dimethyl aminopyridine (0.04g.), and the solution was then stirred at 25° C. for 4 hours. The mixture was diluted with 10 mL of dichloromethane, and was washed with water (1×15 mL), saturated sodium bicarbonate solution (2×15 mL), and brine (1×15 mL). The organic phase was then dried over magnesium sulfate, and filtered through a pad of Celite. Evaporation of the solvent in vacuo afforded an oil, which was purified on silica gel eluting with ethyl acetate/hexanes (50/50), to afford 7-methyl-9-[2-fluoro-6-chlorophenyl]-2,3,6,9-tetrahydo-1,1,4,4-tetraoxide 5H-1,4-Dithiepino[6,5-b]pyridine-8-carboxlic acid 2-[1,2,3,4-tetrahydo-2-napthoyl]oxyethyl ester as a pale yellow solid (0.101 g).

EXAMPLE 6

N-Benzyl-N-methyl glycine 2-bromoethyl ester

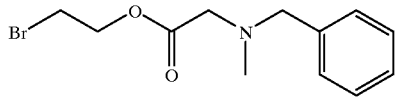

N-Benzyl-N-methyl glycine potassium salt (2.00 g, 11.16 mmol) and 2-Bromo ethanol (2.48 g, 17.86 mmol) was suspended in 20 mL of dichloromethane. To this solution was added 1-(3-dimethylaminopropyl)-3-ethylcarbodiimide hydrochloride (6.40 g, 33.5 mmol) and 4-(dimethylamino) pyridine (1.00 g) and the reaction was stirred at 25° C. overnight. The mixture was diluted with 40 mL of dichloromethane, and was washed with water (1×60 mL), saturated sodium bicarbonate solution (2×60 mL), and brine (1×60 mL). The organic phase was then dried over magnesium sulfate, and filtered through a pad of Celite. Evaporation of the solvent in vacuo afforded an oil, which was purified on silica gel eluting with ethyl acetate to afford N-Benzyl-N-methyl glycine 2-bromoethyl ester as an oil (0.70 g).

B. Assays

EXAMPLE 7

Assay for Inhibition of Nitrendipine Binding

Female, New Zealand white rabbits (1–2 kg) are sacrificed by cervical dislocation, and the heart is immediately removed, cleaned and chopped into small pieces. The tissue is homogenized in 5× times volume of 0.05M Hepes buffer, pH 7.4. The homogenate is centrifuged at 4000g for 10 minutes, and the supernatant is re-centrifuged at 42,000× g for 90 minutes. The resulting membrane pellet is resuspended (0.7 ml/g weight) in 0.05M Hepes, pH 7.4 and stored at 70° C. until used. Each tube of the binding assay contains $^3$H-nitrendipine (0.05–0.50 nM), buffer, membranes (0.10 ml), and test compound in a total volume of 1.0 ml. After 90 minutes at $4 \leq$ C., the bound nitrendipine is separated from the unbound by filtration on Whatman GF/C filters. After rinsing, the filters are dried and counted in a liquid scintillation counter.

Non-specific binding of $^3$H-nitrendipine (that amount bound in the presence of excess unlabelled nitrendipine) is subtracted from the total bound to obtain specifically bound radiolabeled nitrendipine. The amount of specifically bound nitrendipine in the presence of a test compound is compared to that amount bound in the absence of a compound. A percent displacement (or inhibition) can then be calculated.

EXAMPLE 8

Test for Inhibition of Calcium-Dependent Smooth Muscle Contraction

The trachea and the aorta from dogs sacrificed by excess KCI injection are stored overnight at 4° C. in oxygenated Krebs-Henseleit buffer. Tracheal rings, one cartilage segment wide (5–10 mm), are cut starting from the bronchial end. Rings of aorta tissue of the same width are also prepared. After cutting the cartilage, the trachealis muscle tissue and the aorta tissue are suspended in oxygenated Krebs-Henseleit buffer at 37° C. in a 25 ml tissue bath. After a 60-minute equilibration period, the tissues are challenged with 10 μM carbachol. After 5 minutes, the tissues are rinsed and allowed to rest 50 minutes. The tissues are then challenged with 50 mM KCl and, after 30 minutes, the contractions are quantitated. The tissues are then rinsed and re-equilibrated for 50 minutes. Test compounds are then added for 10 minutes, and the tissue is rechallenged with 50 mM KCl. After 30 minutes, the contraction is recorded. A percent inhibition of smooth muscle contraction can then be calculated.

C. Selected Embodiments of the Instant Compounds

Tables 1 and 2 for Formulae Ii and Ij, below, set forth the mass spectra data, the inhibition of nitrendipine binding and inhibition of calcium-dependent smooth muscle contraction for some compounds of Formula I tested.

TABLE 1

Mass Spectra Data and Calcium Channel Antagonist Activity for Compounds 1–66

Formula Ii

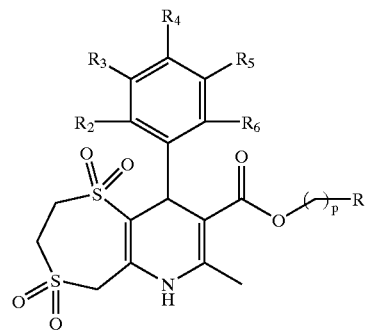

| Compound No. | $R_2$ | $R_3$ | $R_4$ | $R_5$ | $R_6$ | p | R | M + 23 or M + 1 | Nitrendipine Binding Assay $IC_{50}$ nM |
|---|---|---|---|---|---|---|---|---|---|
| 1 | F | H | H | H | Cl | 1 | $CH_2OC(O)CH(CH_2CH_3)_2$ | 600 | 13 |
| 2 | Cl | Cl | H | H | H | 1 | $CH_2OC(O)CH(CH_3)_2$ | 588 | 15 |
| 3 | F | H | H | H | Cl | 1 | $CH_2OC(O)$—PH—$OCH(CH_3)_2$ | 664 | 20 |
| 4 | F | H | H | H | Cl | 1 | $CH_2OC(O)(CH_2)_2CH(CH_3)_2$ | 600 | 20 |
| 5 | F | H | H | H | Cl | 1 | $CH_2OC(O)CH(CH_3)CH_2$—PH | 648 | 33 |
| 6 | F | H | H | H | Cl | 1 | $CH_2OC(O)CH_2CH(CH_3)_2$ | 586 | 35 |
| 7 | F | H | H | H | Cl | 1 | $CH_2OC(O)CH(CH_2)_6$ | 626 | 38 |
| 8 | F | H | H | H | Cl | 1 | $CH_2OC(O)$—PH-3-$OCH_3$ | 636 | 41 |
| 9 | F | H | H | H | Cl | 2 | $CH_2OC(O)$—PH | 620 | 43 |
| 10 | F | H | H | H | Cl | 1 | $CH_2OC(O)$-tetrahydronaphthyl | 660 | 44 |
| 11 | F | H | H | H | Cl | 1 | $CH_2OC(O)$—PH—$CF_3$ | 674 | 48 |
| 12 | F | H | H | H | Cl | 1 | $CH_2OC(O)(CH_2)_2PH$ | 634 | 48 |
| 13 | F | H | H | H | Cl | 1 | PH—$C(O)OCH_3$ | 606 | 48 |
| 14 | F | H | H | H | Cl | 1 | $CH_2OC(O)$-naphthyl | 656 | 50 |
| 15 | F | H | H | H | Cl | 1 | $CH_2OC(O)CH_2N(CH_3)CH_2PH$ | 663 | 50 |
| 16 | F | H | H | H | Cl | 1 | $CH_2OC(O)$—PH-4-CN | 631 | 55 |
| 17 | F | H | H | H | Cl | 3 | $CH_2OC(O)$—PH | 634 | 57 |
| 18 | F | H | H | H | Cl | 1 | $CH_2OC(O)$—PH-3-CN | 631 | 61 |
| 19 | F | H | H | H | Cl | 1 | $CH_2OC(O)$—PH | 606 | 62 |
| 20 | F | H | H | H | Cl | 1 | $CH_2OC(O)$—PH-4-$OCH_3$ | 636 | 69 |
| 21 | H | H | H | Cl | Cl | 1 | dimethyl dioxol-2-one | 586 | 72 |
| 22 | F | H | H | H | Cl | 1 | $CH_2OC(O)CH_2$—PH—$N(CH_3)_2$ | 663 | 80 |
| 23 | F | H | H | H | Cl | 1 | $CH_2OC(O)CH(CH_2)_5$ | 612 | 100 |
| 24 | F | H | H | H | Cl | 1 | $CH_2OC(O)CH_2$—PH—$N(CH_3)_2$ | 649 | 118 |
| 25 | F | H | H | H | Cl | 1 | $CH_2OC(O)CH(CH_3)_2$ | 572 | 143 |
| 26 | F | H | H | H | Cl | 1 | $CH_2OC(O)CH_2N(CH_3)C(O)PH$ | 677 | 153 |
| 27 | F | H | H | H | Cl | 1 | $C(O)O(CH_2)_2PH$ | 620 | 154 |

TABLE 1-continued

Mass Spectra Data and
Calcium Channel Antagonist Activity for Compounds 1–66

Formula Ii

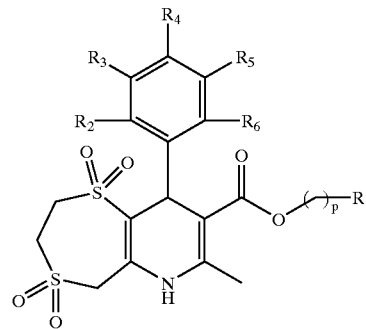

| Compound No. | $R_2$ | $R_3$ | $R_4$ | $R_5$ | $R_6$ | p | R | M + 23 or M + 1 | Nitrendipine Binding Assay $IC_{50}$ nM |
|---|---|---|---|---|---|---|---|---|---|
| 28 | F | H | H | H | Cl | 0 | 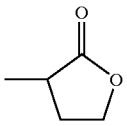 | 542 | 174 |
| 29 | F | H | H | H | Cl | 1 | $CH_2OC(O)CH(NHC(O)OC(CH_3)_3)$ $(CH_2)_4NHC(O)OCH_2PH$ | — | 175 |
| 30 | F | H | H | H | Cl | 2 | $CH_2OC(O)CH(CH_3)_2$ | 586 | 176 |
| 31 | Cl | Cl | H | H | H | 2 | 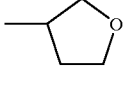 | 586 | 194 |
| 32 | F | H | H | H | Cl | 1 | $CH_2OC(O)CH(CH_3)_2$ | 572 | 220 |
| 33* | Cl | H | H | H | F | 2 | $C(O)OPH$ | 620 | 276 |
| 34 | F | H | H | H | Cl | 1 | $C(O)OCH_2PH$ | 606 | 279 |
| 35 | Cl | H | H | H | F | 1 | $C(O)OPH$ | 592 | 336 |
| 36 | Cl | H | H | H | F | 2 | $CH_2OC(O)CH_3$ | 558 | 340 |
| 37 | F | H | H | H | Cl | 1 | $C(O)OC(CH_3)_3$ | 572 | 356 |
| 38 | F | H | H | H | Cl | 1 | $CH_2OC(O)CH(NHCOPH)CH_2PH$ | 753 | 358 |
| 39 | F | H | H | H | Cl | 1 | 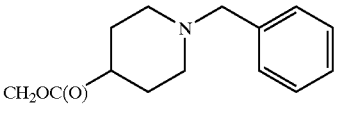 | 703 | 358 |
| 40 | F | H | H | H | Cl | 1 | $CH_2OC(O)CH$ $(NHC(O)OC(CH_3)_3)CH(CH_3)_2$ | 701 | 405 |
| 41 | F | H | H | H | Cl | 1 | 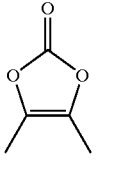 | 570 | 417 |
| 42 | Cl | H | H | H | F | 1 | $C(O)O(CH_2)_2N(CH_3)CH_2PH$ | 663 | 420 |
| 43 | H | H | H | Cl | Cl | 0 | 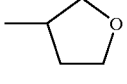 | 558 | 456 |

TABLE 1-continued

Mass Spectra Data and
Calcium Channel Antagonist Activity for Compounds 1–66

Formula Ii

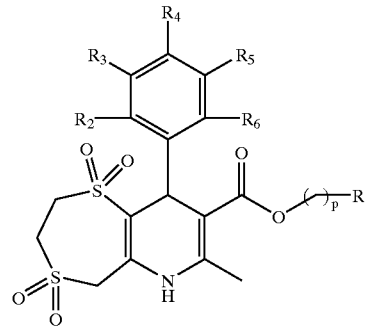

| Compound No. | $R_2$ | $R_3$ | $R_4$ | $R_5$ | $R_6$ | p | R | M + 23 or M + 1 | Nitrendipine Binding Assay $IC_{50}$ nM |
|---|---|---|---|---|---|---|---|---|---|
| 44 | F | H | H | H | Cl | 1 | CH₂OC(O)-3-pyridyl | 585 | 505 |
| 45 | F | H | H | H | Cl | 1 | CH₂OC(O)CH(N(CH₃)₂)CH₂PH | 677 | 541 |
| 46 | F | H | H | H | Cl | 1 | CH₂OC(O)-4-pyridyl | 607 | 760 |
| 47 | F | H | H | H | Cl | 1 | CH₂NHC(O)OC(CH₃)₃ | 601 | 768 |
| 48 | F | H | H | H | Cl | 1 | CH₂OC(O)CH₃ | 544 | 898 |
| 49 | F | H | H | H | Cl | 1 | CH₂OC(O)CH₂NHC(O)OC(CH₃)₂) | 659 | 946 |
| 50 | F | H | H | H | Cl | 1 | CH₂OH | 502 | 1000 |
| 51 | F | H | H | H | Cl | 2 | CH₂OH | 516 | 1208 |
| 52 | F | H | H | H | Cl | 1 | CH₂OC(O)CH₂N(CH₃)₂ | 587 | 1233 |
| 53 | Cl | H | H | H | F | 2 | 3-methyl-γ-butyrolactone | 570 | 1688 |
| 54 | F | H | H | H | Cl | 2 | CH₂OC(O)CH₃ | 558 | 2122 |
| 55 | F | H | H | H | Cl | 1 | CH₂NHC(O)PH | 605 | 2264 |
| 56* | F | H | H | H | Cl | 1 | CH₂OC(O)CH(CH₃)₂ | 572 | 2323 |
| 57 | F | H | H | H | Cl | 1 | CH₂OC(O)C(CH₃)₃ | 586 | 3700 |
| 58 | F | H | H | H | Cl | 1 | C(O)N(CH₂CH₃)₂ | 571 | 4238 |
| 59 | F | H | H | H | Cl | 1 | CH₂NH₂ | 501 | 4841 |
| 60* | F | H | H | H | Cl | 1 | CH₂OC(O)CH(N*H₂)(CH₃)₂ | 601 | 5800 |
| 61 | F | H | H | H | Cl | 1 | C(O)NH₂ | 515 | 6986 |
| 62 | F | H | H | H | Cl | 1 | CH₂OC(O)-γ-butyrolactonyl | 614 | 19370 |

TABLE 1-continued

Mass Spectra Data and
Calcium Channel Antagonist Activity for Compounds 1–66

Formula Ii

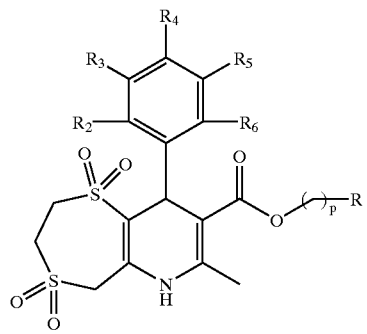

| Compound No. | R$_2$ | R$_3$ | R$_4$ | R$_5$ | R$_6$ | p | R | M + 23 or M + 1 | Nitrendipine Binding Assay IC$_{50}$ nM |
|---|---|---|---|---|---|---|---|---|---|
| 63 | F | H | H | H | Cl | 1 | CH$_2$OC(O)(CH$_2$)$_2$–N(piperidine) | 641 | 49000 |
| 64* | F | H | H | H | Cl | 1 | CH$_2$OC(O)CH(N*H$_2$)(CH$_2$)$_4$NH$_2$ | 608 | 51000 |
| 65 | F | H | H | H | Cl | 1 | CH$_2$OC(O)CH$_2$NH$_2$ | 559 | 150000 |
| 66 | Cl | H | H | H | F | 1 | COOH | 516 | 316000 |

*enantiomer/chiral atom

TABLE 2

Mass Spectra Data and
Calcium Channel Antagonist Activity for Compounds 67–77

Formula Ij

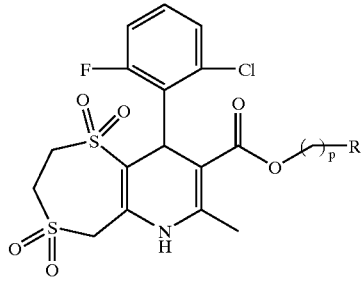

| Compound No. | p | R | M + 23 | Nitrendipine Binding Assay IC$_{50}$ nM |
|---|---|---|---|---|
| 67 | 1 | CH$_2$OC(O)—PH—OCH(CH$_3$)$_2$ | 678 | 40 |
| 68 | 1 | CH$_2$OC(O)—PH—CN | 645 | 49 |
| 69 | 1 | CH$_2$OC(O)CH$_2$—PH—N(CH$_3$)$_2$ | 677 | 55 |
| 70 | 1 | CH$_2$OC(O)CH(CH$_2$)$_5$ | 626 | 65 |
| 71 | 1 | CH$_2$OC(O)—PH—CF$_3$ | 688 | 85 |
| 72 | 1 | CH$_2$OC(O)C(CH$_3$)$_3$ | 600 | 108 |
| 73 | 1 | CH$_2$OC(O)CH(CH$_3$)$_2$ | 586 | 203 |
| 74* | 1 | CH$_2$OC(O)CH(N*HC(O)OC(CH$_3$)$_3$)CH(CH$_3$)$_2$ | 715 | 299 |
| 75 | 1 | CH$_2$OC(O)CH(NHC(O)PH)CH$_2$PH | 767 | 706 |
| 76 | 1 | CH$_2$OC(O)CH$_3$ | 558 | 754 |
| 77 | 1 | CH$_2$OH | 516 | 1337 |

Table 3 sets forth the mass spectra data and the structures of additional compounds of the instant invention.

TABLE 3
Mass Spectra Data for Compounds 78–117
| No. | (M + 23/M + 1/M − 1) |
|---|---|
| 78 | 455 |
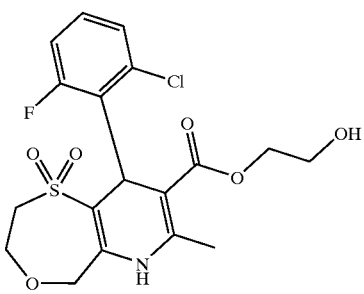
| | |
|---|---|
| 79 | 534 |
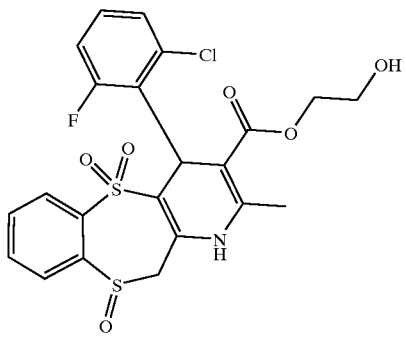
| | |
|---|---|
| 80 | 550 |
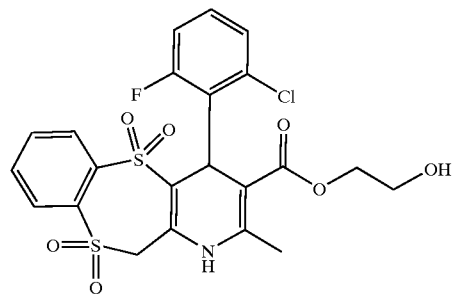
| | |
|---|---|
| 81 | 592 |
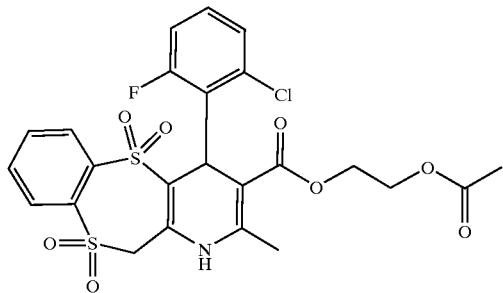

TABLE 3-continued
Mass Spectra Data for Compounds 78–117
| No. | (M + 23/M + 1/M − 1) |
|---|---|
| 82 | 558 |
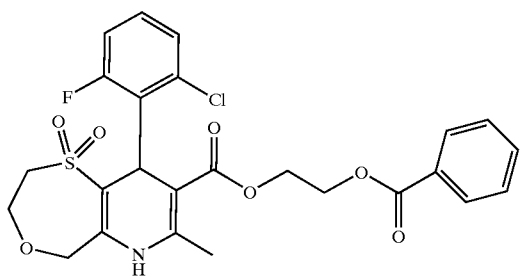
| 83 | 654 |
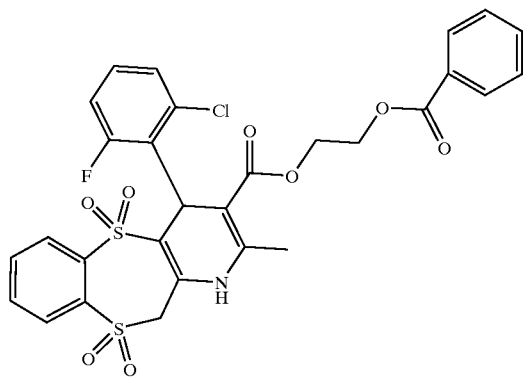
| 84 | 564 |
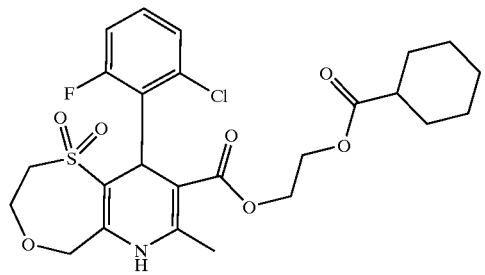
| 85 | 660 |
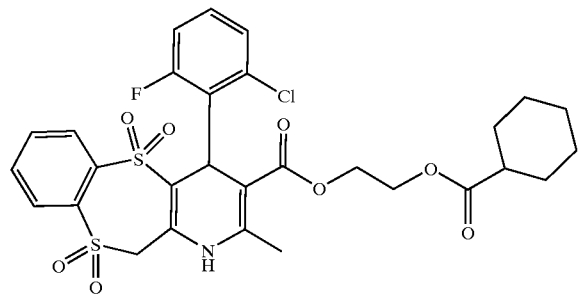

TABLE 3-continued

Mass Spectra Data for Compounds 78–117

| No. | (M + 23/M + 1/M − 1) |
|---|---|
| 86 | 649 |
| 87 | 527 |
| 88 | 496 |
| 89 | 522 |

TABLE 3-continued
Mass Spectra Data for Compounds 78–117
| No. | (M + 23/M + 1/M − 1) |
|---|---|
| 90 | 524 |
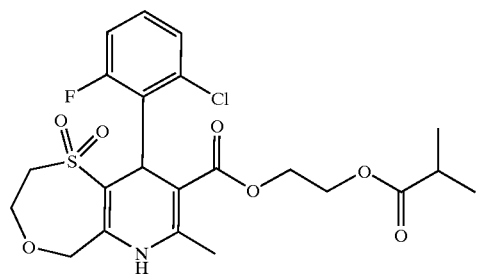
| 91 | 620 |
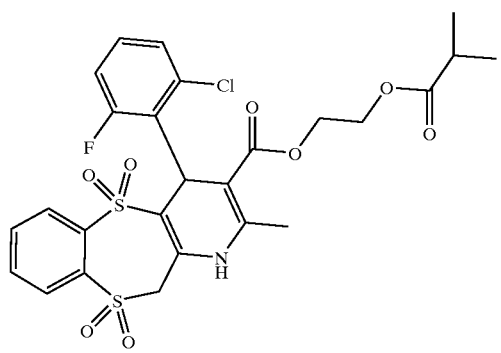
| 92 | 634 |
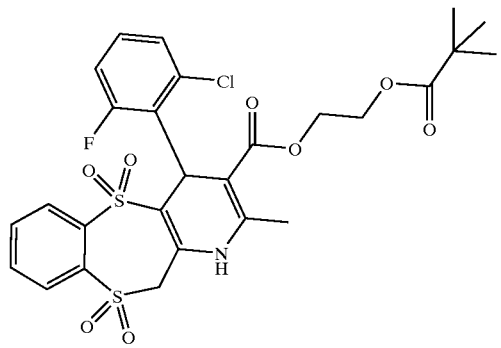
| 93 | 600 |
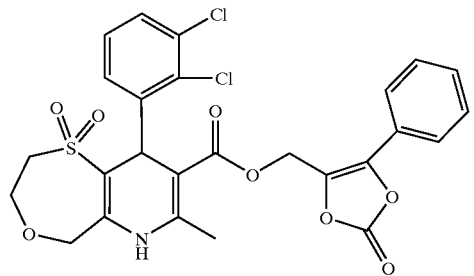

TABLE 3-continued
Mass Spectra Data for Compounds 78–117
| No. | (M + 23/M + 1/M − 1) |
|---|---|
| 94 | 538 |
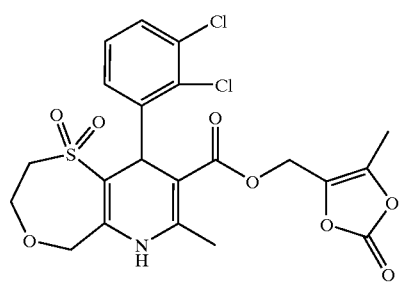
| 95 | 436 |
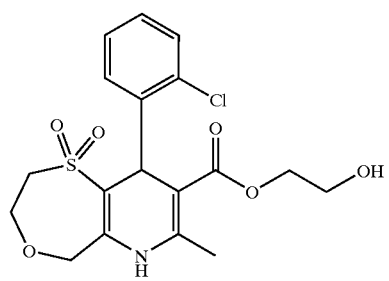
| 96 | 554 |
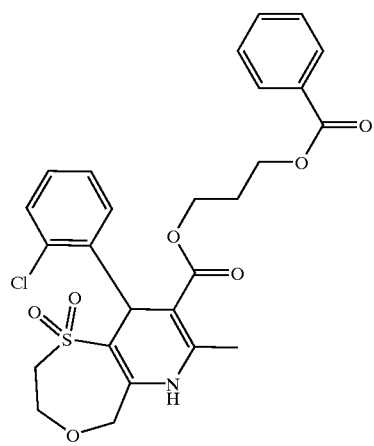
| 97 | 564 |
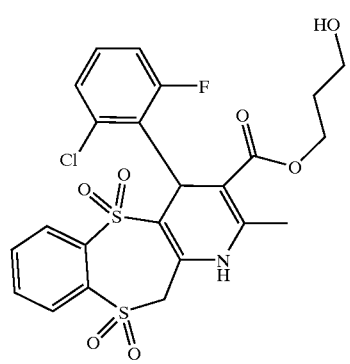

TABLE 3-continued
Mass Spectra Data for Compounds 78–117
| No. | (M + 23/M + 1/M − 1) |
|---|---|
| 98 | 668 |
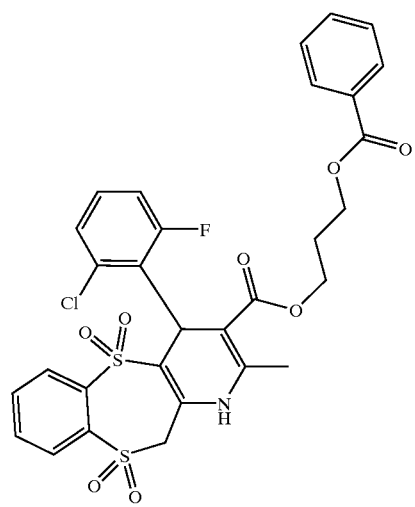
| 99 | 426 |
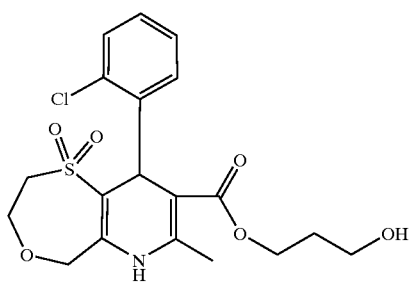
| 100 | 506 |
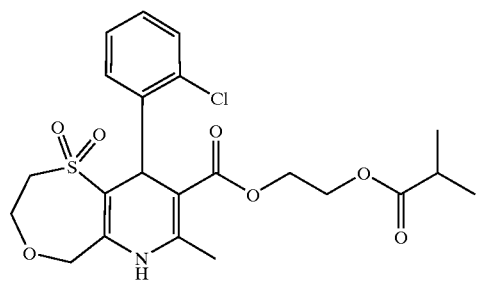
| 101 | 479 |
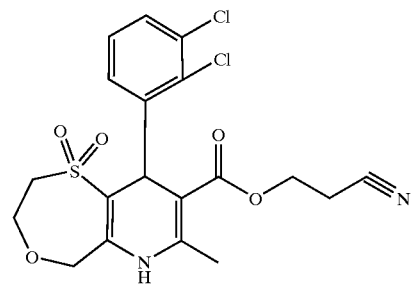

TABLE 3-continued

Mass Spectra Data for Compounds 78–117

| No. | (M + 23/M + 1/M − 1) |
|---|---|
| 102 | 618 |
| 103 | 590 |
| 104 | 680 |
| 105 | 439 |

TABLE 3-continued

Mass Spectra Data for Compounds 78–117

| No. | (M + 23/M + 1/M − 1) |
|---|---|
| 106 | 467 |
| 107 | 467 |
| 108 | 653 |
| 109 | 668 |

TABLE 3-continued
Mass Spectra Data for Compounds 78–117
| No. | (M + 23/M + 1/M − 1) |
|---|---|
| 110 | 762 |
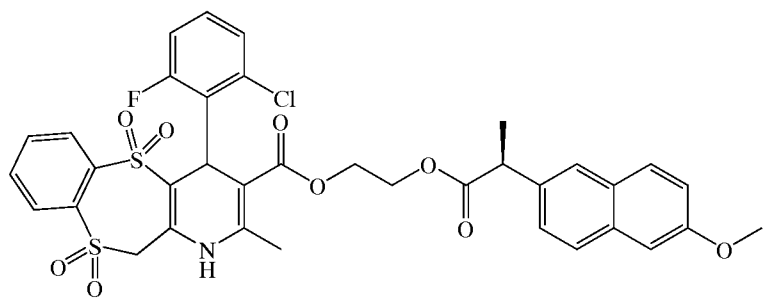
| 111 | 738 |
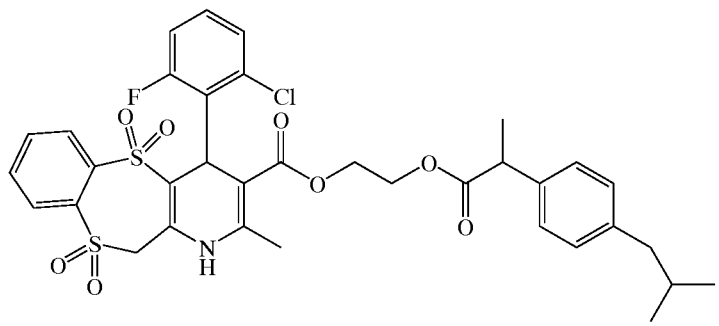
| 112 | 738 |
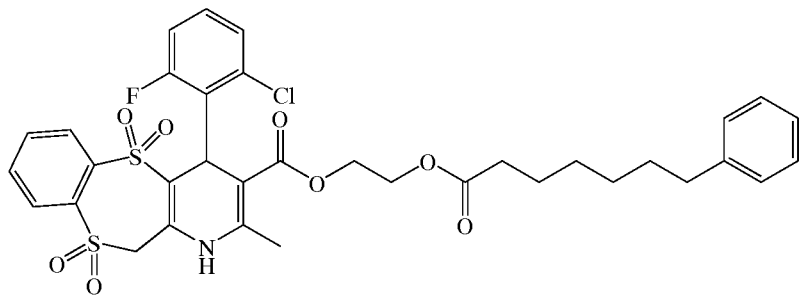
| 113 | 780 |
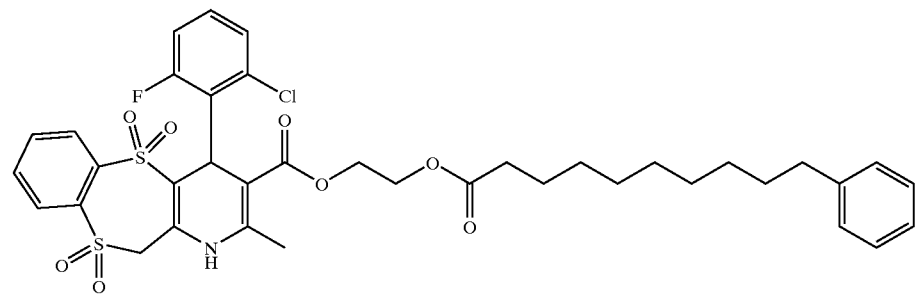

TABLE 3-continued
Mass Spectra Data for Compounds 78–117
| No. | (M + 23/M + 1/M − 1) |
|---|---|
| 114 | 680 |
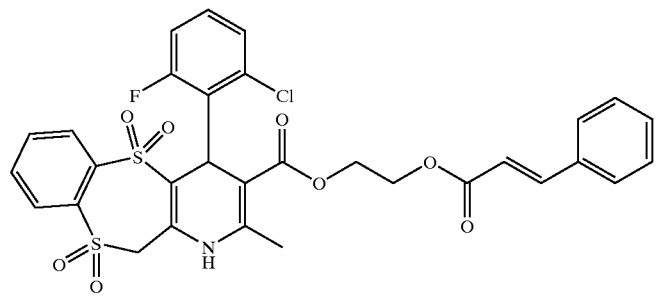
| 115 | 618 |
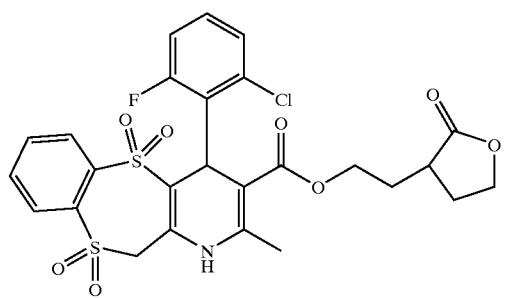
| 116 | 530 |
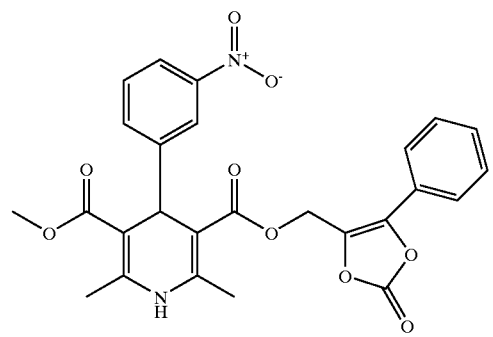
| 117 | 563 |
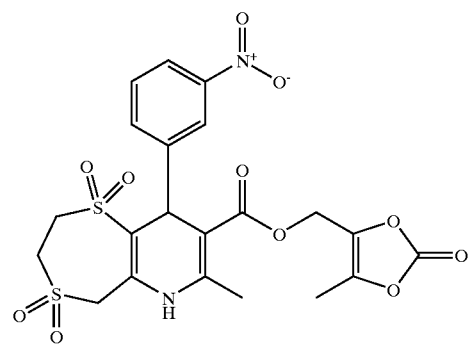

Table 4, wherein $R_1$ is as described above, sets forth selected representative dihydropyridine soft drug groups of the instant invention.

TABLE 4

Representative Dihydropyridine Soft Drug Groups

| Group No. | Dihydropyridine Soft Drugs |
|---|---|
| 1 | isopropyl ester / 3-nitrophenyl dihydropyridine-OR$_1$ |
| 2 | 3-oxobutyl ester / 3-nitrophenyl dihydropyridine-OR$_1$ |
| 3 | HO-carbonyl / 3-nitrophenyl dihydropyridine-OR$_1$ |
| 4 | methyl ester / 2-nitrophenyl dihydropyridine-OR$_1$ |
| 5 | 2-(methylthio)ethyl ester / 3-nitrophenyl dihydropyridine-OR$_1$ |
| 6 | ethyl ester / 2-(trifluoromethyl)phenyl dihydropyridine-OR$_1$ |
| 7 | methyl ester / 3-nitrophenyl dihydropyridine-OR$_1$ |
| 8 | phenylsulfonyl / 3-nitrophenyl dihydropyridine-OR$_1$ |
| 9 | sec-butyl ester / 3-nitrophenyl dihydropyridine-OR$_1$ |
| 10 | ethyl ester / 3-nitrophenyl dihydropyridine-OR$_1$ |

TABLE 4-continued

Representative Dihydropyridine Soft Drug Groups

| Group No. | Dihydropyridine Soft Drugs |
|---|---|
| 11 | |
| 12 | |
| 13 | |
| 14 | |
| 15 | |
| 16 | |
| 17 | |
| 18 | |
| 19 | |
| 20 | |

TABLE 4-continued

Representative Dihydropyridine Soft Drug Groups

| Group No. | Dihydropyridine Soft Drugs |
|---|---|
| 21 | |
| 22 | |
| 23 | |
| 24 | |
| 25 | |
| 26 | |
| 27 | |
| 28 | |

TABLE 4-continued

Representative Dihydropyridine Soft Drug Groups

| Group No. | Dihydropyridine Soft Drugs |
|---|---|
| 29 | |
| 30 | |
| 31 | |
| 32 | |
| 33 | |
| 34 | |
| 35 | |
| 36 | |

TABLE 4-continued
Representative Dihydropyridine Soft Drug Groups
| Group No. | Dihydropyridine Soft Drugs |
|---|---|
| 37 | 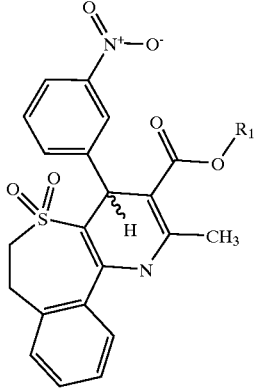 |
| 38 | 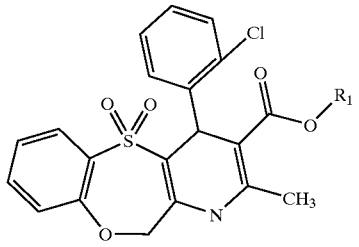 |
| 39 | 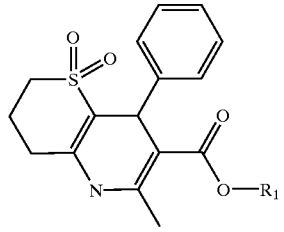 |
| 40 | 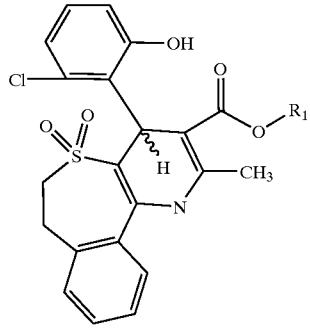 |
| 41 |  |
| 42 |  |
| 43 |  |
| 44 |  |
| 45 |  |

TABLE 4-continued

Representative Dihydropyridine Soft Drug Groups

| Group No. | Dihydropyridine Soft Drugs |
|---|---|
| 46 | (structure) |
| 47 | (structure) |
| 48 | (structure) |
| 49 | (structure) |
| 50 | (structure) |
| 51 | (structure) |
| 52 | (structure) |
| 53 | (structure) |
| 54 | (structure) |
| 55 | (structure) |
| 56 | (structure) |
| 57 | (structure) |

TABLE 4-continued

Representative Dihydropyridine Soft Drug Groups

| Group No. | Dihydropyridine Soft Drugs |
|---|---|
| 58 | (structure) |
| 59 | (structure) |
| 60 | (structure) |
| 61 | (structure) |
| 62 | (structure) |
| 63 | (structure) |
| 64 | (structure) |
| 65 | (structure) |
| 66 | (structure) |

TABLE 4-continued
Representative Dihydropyridine Soft Drug Groups
| Group No. | Dihydropyridine Soft Drugs |
|---|---|
| 67 | 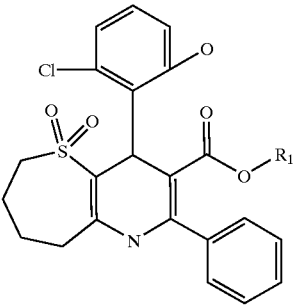 |
| 68 | 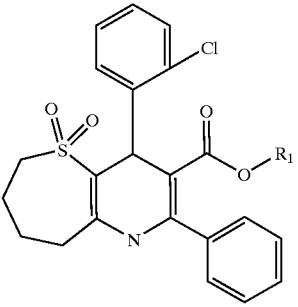 |
| 69 | 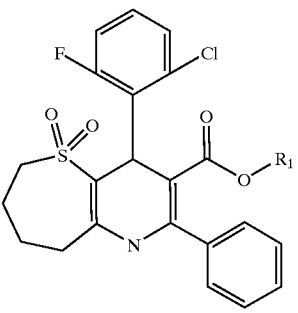 |
| 70 | 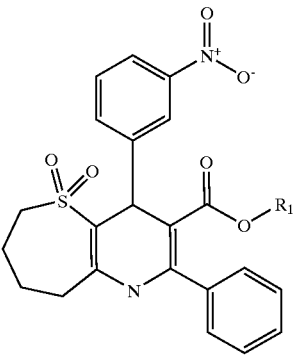 |
| 71 | 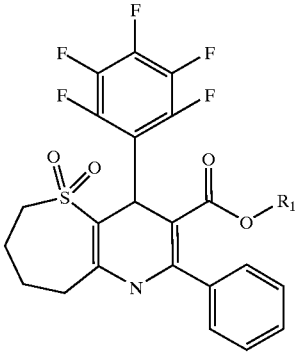 |
| 72 | 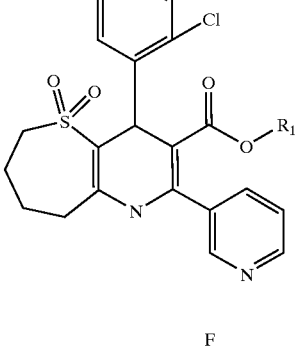 |
| 73 | 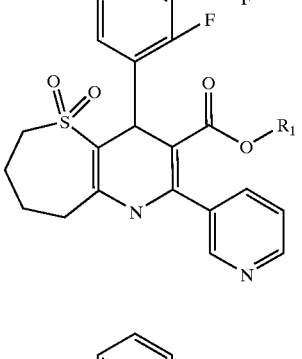 |
| 74 | 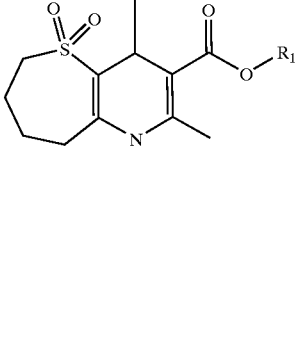 |

TABLE 4-continued

Representative Dihydropyridine Soft Drug Groups

| Group No. | Dihydropyridine Soft Drugs |
|---|---|
| 75 | |
| 76 | |
| 77 | |
| 78 | |
| 79 | |
| 80 | |
| 81 | |

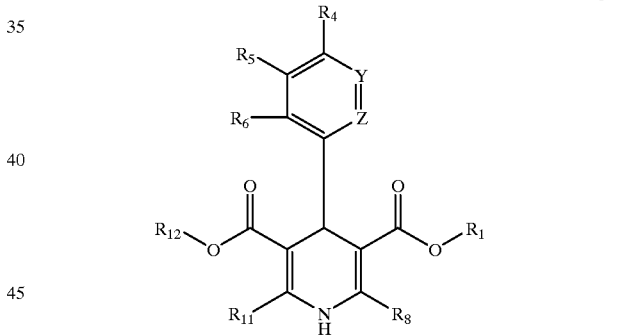

What is claimed is:

1. A compound having Formula (Ig) or a pharmaceutically acceptable salt thereof, wherein Ig (a) Z is N or $CR_2$;
(b) Y is N or $CR_3$;
(c) $R_1$ is selected from -alkyl-OH, alkylamine, lactone, cyclic carbonate, alkyl-substituted cyclic carbonate, aryl-substituted cyclic carbonate, -aryl-C(O)OR', -alkyl-aryl-C(O)OR', -alkyl-OC(O)R', -alkyl-C(O)R', -alkyl-C(O)OR', -alkyl-N(R")C(O)R', and -alkyl-N(R") C(O)OR'OR', provided that when $R_{12}$ is -alkyl-OH then $R_1$ cannot be -alkyl-OH and when $R_{12}$ is alkylamine then $R_1$ cannot be alkylamine;
(d) $R_2$, $R_3$, $R_4$, $R_5$ and $R_6$ are independently selected from the group consisting of hydrogen, OH, halogen, cyano, $NO_2$, alkyl, $C_{1-8}$ alkoxy, difluoromethoxy, difluoromethylthio, trifluoromethyl and oxadiazole (formed by $R_2$ and $R_3$);
(e) $R_8$ is selected from the group consisting of hydrogen, amino, and alkyl;
(f) $R_{11}$ is selected from the group consisting of hydrogen, amino, and alkyl; and (g) $R_{12}$ is selected from hydrogen, -alkyl-OH, alkylamine, lactone, cyclic carbonate, alkyl-substituted cyclic carbonate, aryl-substituted cyclic carbonate, -aryl-C(O)OR', -alkyl-OC(O)R', -alkyl-C(O)R', -alkyl-C(O)OR', -alkyl-N(R")C(O)R', -alkyl-N(R")C(O)OR', -alkyl-S—R', alkyl, aryl-substituted alkyl, aryl, —(CH$_2$)$_2$N(CH$_3$)CH$_2$[PH]Ph, —CH$_2$CH$_2$–N(Me)—CH$_2$-heteroaryl, 3-piperidyl, N-substituted 3-piperidyl, and N-substituted 2-pyrrolidinyl methylene), provided that when $R_1$ is -alkyl-OH then $R_{12}$ cannot be -alkyl-OH and when $R_1$ is alkylamine then $R_{12}$ cannot be alkylamine, wherein (i) R' and R" are independently selected from hydrogen, amino, alkyl, aryl, aryl-fused cycloalkyl and heterocyclyl, the amino, alkyl, aryl, aryl-fused cycloalkyl and heterocyclyl being optionally substituted with halogen, cyano, NO$_2$, lactone, amino, alkylamino, aryl-substituted alkylamino, amide, carbamate, carbamoyl, cyclic carbonate, alkyl, halogen-substituted alkyl, arylalkyl, alkoxy, heterocyclyl and/or aryl (the aryl being optionally substituted with OH, halogen, cyano, NO$_2$, alkyl, amino, dimethylamino, alkoxy, alkylsulfonyl, C$_{1-4}$ carboalkoxy, alkylthio and/or trifluoromethyl);

(ii) the alkyl may be substituted with alkoxy, C$_2$–C$_8$ alkanoyloxy, phenylacetyloxy, benzoyloxy, hydroxy, halogen, p-tosyloxy, mesyloxy, amino, carboalkoxy, and/or NR$^{IV}$R$^V$, wherein R$_{IV}$ and R$_V$ are independently selected from hydrogen, alkyl, phenyl, benzyl and phenethyl, or R$_{IV}$ and R$_V$ together form a heterocyclic ring selected from the group consisting of piperidino, pyrrolidino, morpholino, thiomorpholino, piperazino, 2-thieno, 3-thieno and an N-substituted derivative of the heterocyclic rings (the N-substituted derivative being substituted with hydrogen, alkyl, benzyl, benzhydryl and/or phenyl optionally substituted with hydrogen, NO$_2$, halogen, alkyl, alkoxy and/or trifluoromethyl); and (iii) the N-substituted 3-piperidyl and the N-substituted 2-pyrrolidinyl methylene are optionally substituted with alkyl or benzyl.

2. The compound of claim 1, wherein $R_{12}$ is selected from hydrogen, alkyl, and aryl-substituted alkyl.

3. The compound of claim 2, wherein $R_{12}$ is selected from hydrogen, —CH$_3$, —CH$_2$CH$_3$, —CH(CH$_3$)$_2$, —CH(CH$_3$)CH$_2$CH$_3$, —CH$_2$CH$_2$—O—CH$_3$, —CH$_2$CH$_2$—S—CH$_3$, cyclopentane and benzyl.

4. The compound of claim 1, wherein Z is CR$_2$.

5. The compound of claim 1, wherein Y is CR$_3$.

6. The compound of claim 1 which is 3,5-pyridinedicarboxylic acid, 1,4-dihydro-2,6-dimethyl-4-(3-nitrophenyl)-, 3-methyl 5-(tetrahydro-2-oxo-3-furanyl) ester.

7. The compound of claim 1 which is 3,5-pyridinedicarboxylic acid, 1,4-dihydro-2,6-dimethyl-4-(3-nitrophenyl)-, 3-methyl 5-[2-(tetrahydro-2-oxo-3-furanyl) ethyl] ester.

8. The compound of claim 1 which is 3,5-pyridinedicarboxylic acid, 1,4-dihydro-2,6-dimethyl-4-(3-nitrophenyl)-, 3-methyl 5-[(5-methyl-2-oxo-1,3-dioxol-4-yl)methyl] ester.

9. The compound of claim 1 which is 3,5-pyridinedicarboxyllic acid, 1,4-dihydro-2,6-dimethyl-4-(3-nitrophenyl)-, 3-methyl 5-[(2-oxo-5-phenyl-1,3-dioxol-4-yl) methyl] ester.

10. A pharmaceutical composition comprising the compound of claim 1 or a pharmaceutically acceptable salt thereof and a pharmaceutically acceptable carrier.

11. A method of treating a subject suffering from asthma whose alleviation is mediated by the reduction of calcium ion influx into cells whose action contribute to the disorder, which method comprises administering to the subject a therapeutically effective dose of the pharmaceutical composition of claim 10.

* * * * *